(12) United States Patent
Snedeker et al.

(10) Patent No.: US 10,959,829 B2
(45) Date of Patent: Mar. 30, 2021

(54) DEVICE FOR TENDON AND LIGAMENT RECONSTRUCTION

(71) Applicant: UNIVERSITAT ZURICH, Zurich (CH)

(72) Inventors: Jess G. Snedeker, Zurich (CH); Xiang Li, Zumikon (CH); Elias Bachmann, Meilen (CH); Sandra Franco Fucentese, Volketswil (CH)

(73) Assignee: UNIVERSITAT ZURICH, Zurich (CH)

( * ) Notice: Subject to any disclaimer, the term of this patent is extended or adjusted under 35 U.S.C. 154(b) by 293 days.

(21) Appl. No.: 15/542,936

(22) PCT Filed: Jan. 12, 2016

(86) PCT No.: PCT/EP2016/025001
§ 371 (c)(1),
(2) Date: Apr. 24, 2018

(87) PCT Pub. No.: WO2016/113142
PCT Pub. Date: Jul. 21, 2016

(65) Prior Publication Data
US 2019/0117375 A1    Apr. 25, 2019

(30) Foreign Application Priority Data
Jan. 12, 2015    (EP) .................................. 15150864

(51) Int. Cl.
*A61F 2/08*    (2006.01)
(52) U.S. Cl.
CPC ....... *A61F 2/0811* (2013.01); *A61F 2002/087* (2013.01); *A61F 2002/0829* (2013.01); *A61F 2002/0882* (2013.01); *A61F 2240/001* (2013.01)

(58) Field of Classification Search
CPC ............ A61F 2/0811; A61F 2002/0882; A61F 2002/087; A61F 2002/0852; A61F 2002/0858; A61F 2002/0864; A61F 2002/0823
See application file for complete search history.

(56) References Cited

U.S. PATENT DOCUMENTS

| | | | |
|---|---|---|---|
| 8,535,377 B2 * | 9/2013 | Myers | A61B 17/0401 623/13.14 |
| 2006/0095130 A1 | 5/2006 | Caborn et al. | |
| 2012/0165866 A1 | 6/2012 | Kaiser et al. | |
| 2014/0303676 A1 | 10/2014 | Stroncek et al. | |

FOREIGN PATENT DOCUMENTS

| | | |
|---|---|---|
| CN | 201542777 | 8/2010 |
| CN | 102481187 | 5/2012 |
| CN | 102871775 | 1/2013 |
| CN | 103784172 | 2/2014 |
| EP | 1297794 | 4/2003 |
| EP | 1491162 | 12/2004 |
| EP | 2238944 | 10/2010 |
| WO | WO2014/076147 | 5/2014 |

* cited by examiner

*Primary Examiner* — Brian A Dukert
(74) *Attorney, Agent, or Firm* — JMB Davis Ben-David

(57) ABSTRACT

The invention relates to a medical implant device for attaching or re-attaching a flexible graft to a bone, comprising: at least a first insert comprising a synthetic osteoconductive and/or osteoinductive material, and a flexible graft, wherein the flexible graft is connected to the at least one insert, particularly prior to surgical implantation of the medical implant device.

20 Claims, 19 Drawing Sheets

Figure 1:
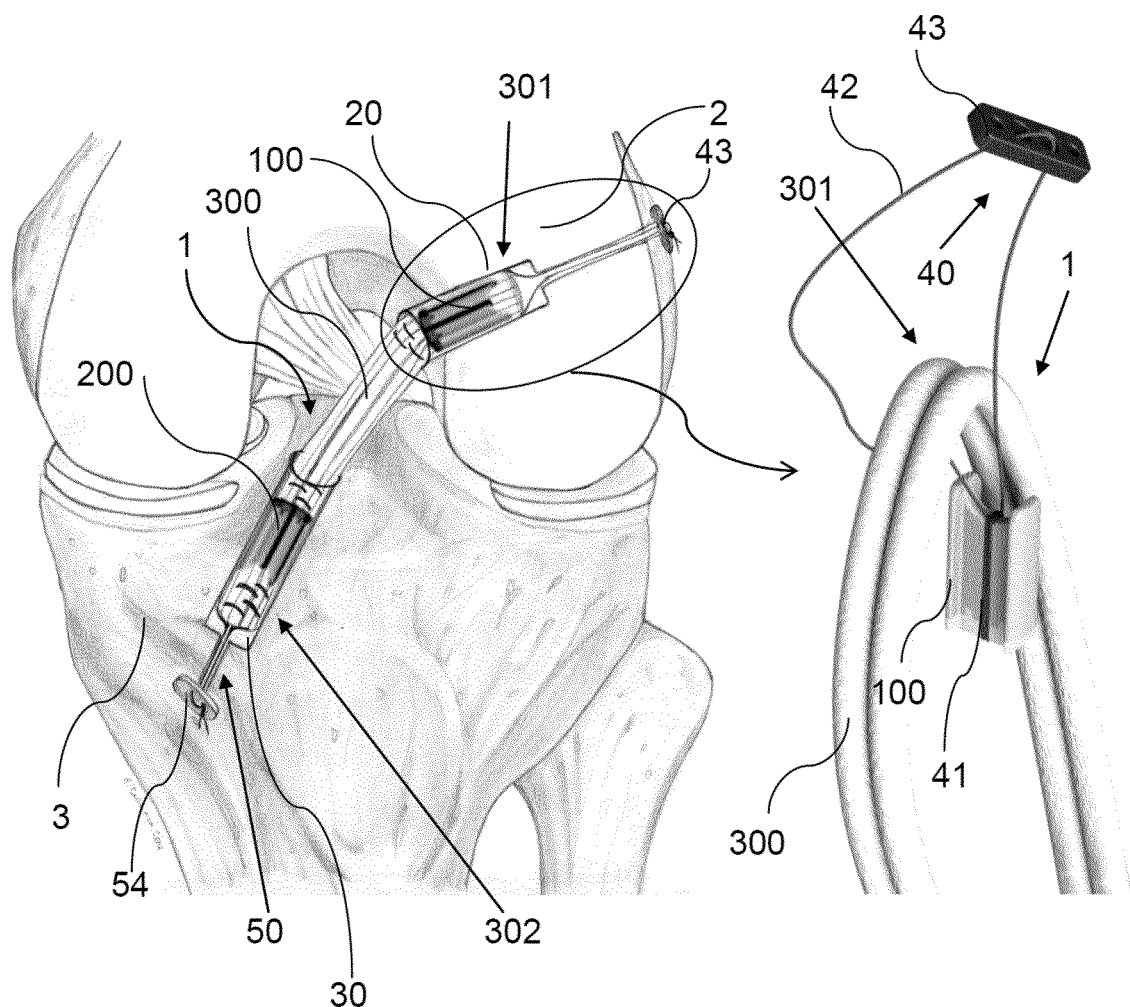

Fig. 10
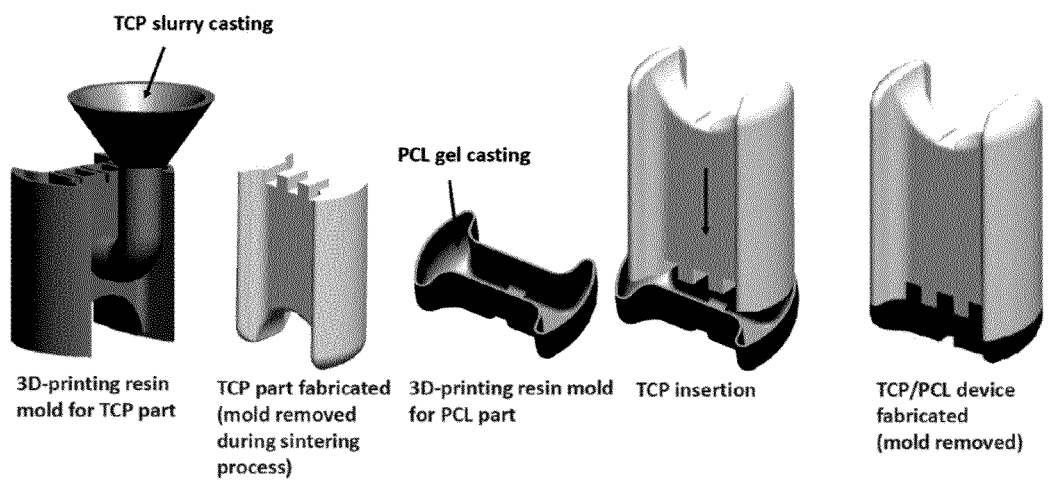
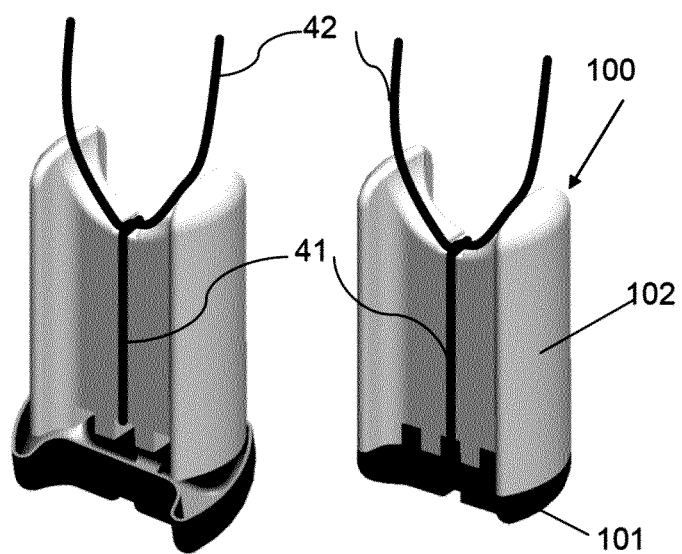

Fig. 31
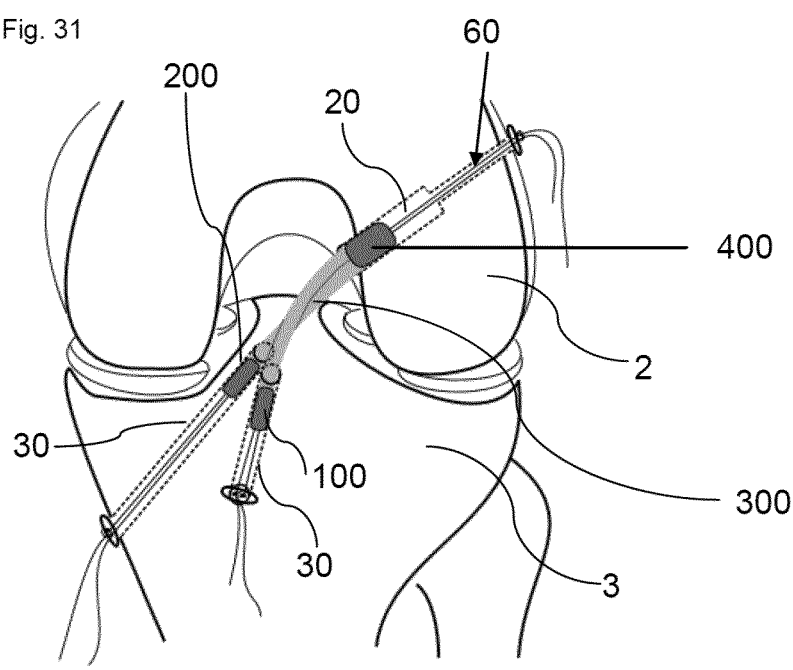
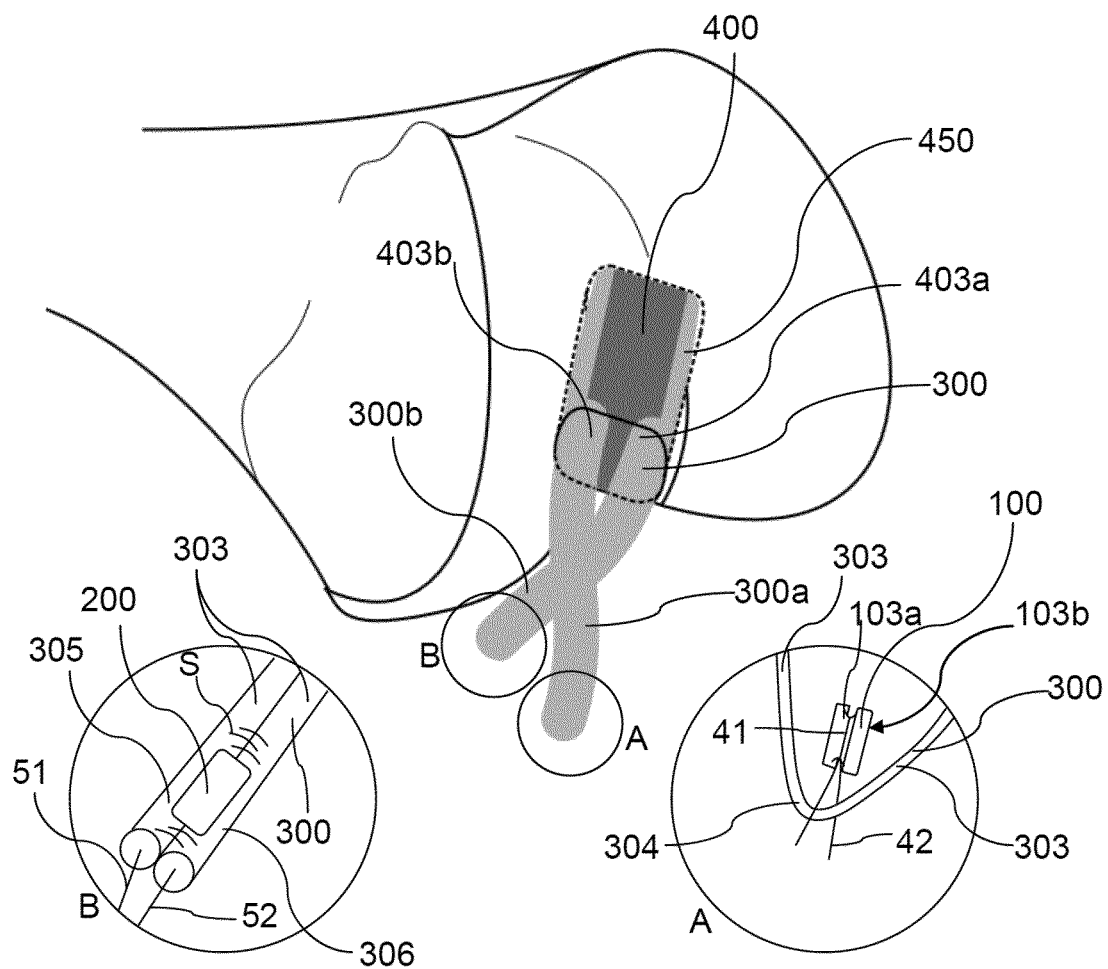

DEVICE FOR TENDON AND LIGAMENT RECONSTRUCTION

CROSS-REFERENCE TO RELATED APPLICATIONS

This is the U.S. National Stage of International Application No. PCT/EP2016/025001 filed Jan. 12, 2016, which was published in English under PCT Article 21(2), and which in turn claims the benefit of European Patent Application No. 15150864.5 filed Jan. 12, 2015.

SPECIFICATION

The invention relates to a medical implant device for fixing a flexible graft, particularly in the form of an artificial or a natural ligament or an artificial or a natural tendon, to a bone, preferably to a human bone.

Due to its anatomical location, the anterior cruciate ligament (ACL) is subjected to potentially extreme forces during sports and other physical activities. Rupture of the ACL has been counted as the most frequent and severe of ligament injuries. It has been estimated that there are around 250,000 (or 1 in 3,000 in the general population) patients per year diagnosed with ACL disruption in the United States, with approximately 75,000 performed surgical reconstruction annually. In Switzerland, there are around 6,000 ACL reconstructions each year. Although numerous and diverse surgical options, including autografts, allografts, xenografts, or synthetic grafts, for ACL reconstruction have been practiced for the restoration of knee joint function, unavoidable drawbacks exist for each approach, such as donor site morbidity, disease transmission, immune response, ligament laxity, mechanical mismatch, and so on.

Clinically implemented graft fixation methods largely rely on bone ingrowth to provide long term ligament stability, with many requiring bone ingrowth to a non-osteoconductive graft. The non-osteoconductive nature of the graft material often critically limits the success of ACL repair. Failure of timely bone ingrowth can lead to "bone tunnel expansion", and ultimately a failed reconstruction that may necessitate a revision surgery with large cost and burden to the patient. To avoid bone tunnel expansion and to achieve effective attachment of an ACL graft within the bone tunnel, sufficient surface contact between the graft and bone, as well as favorable biomechanical/biological stimulation are essential. Although some fixation methods, such as interference screws, can be adopted to anchor the ACL scaffold into bone tunnel, these often impose a decidedly non-physiological barrier to healing.

Many approaches to achieve improved and more rapid integration of an implanted graft to the host bone have been attempted by biomedical device manufacturers and orthopaedic surgeons. One main strategy has been to provide appropriate cellular cues that stimulate a healing response between ligamentous graft and the surrounding bone tunnel. Due to favorable properties regarding osteoconductivity and bioresorption, bone cements, such as brushite calcium phosphate cement (CPC) or tricalcium phosphate (TCP), have been successfully demonstrated to augment the peri-tendon "bone-like" volume at time of implantation, with promoted secondary bone ingrowth at the healing interface that can significantly enhance graft integration [1, 2]. Cell based therapies have also been employed [3, 4], as have bioactive factors such as recombinant BMP-2 [5, 6].

All of these approaches attempt to induce more rapid healing, aimed at avoiding the loss of graft tension in early postoperative stages that often underlies a failed reconstruction. Loss of tension in the replacement ligament can come from a variety of factors, but poor/slow graft integration to the patient's bone is widely considered to be the chief culprit. To accelerate bone integration and promote ligament tension, many knee surgeons often recommend a "bone-tendon-bone autograft". This graft is extracted from the patient's own kneecap by cutting "bone blocks" with a surgical saw. While the transplanted bone blocks at the end of the ligament graft grow quickly into the bone of the knee, the graft extraction can be very painful and is a major cause of patient dissatisfaction. For non-professional athletes, doctors thus often employ a less painful procedure, e.g. a hamstring autograft, that achieves a substantially less stable reconstruction without cutting of bone blocks. The inferior mechanical stability of these grafts can be attributed to the fact that hamstring tendon is slow to grow into the bone, and in the meantime the graft can elongate and loosen. By the time the healing phase is complete, a ligament reconstruction using hamstring autograft is often too slack to ensure normal joint stability. This lack of stability is widely cited as responsible for "secondary osteoarthritis" of the knee—a condition leading to a large number of total joint replacement surgeries.

Based on the above, the problem underlying the present invention is to provide a medical implant device that allows one to replace tendons or ligaments in a more painless manner with an increased stability of the flexible graft replacing said tendon or ligament.

This problem is solved by a medical implant device having the features of claim 1. Preferred embodiments are stated in the sub claims and/or are described below. In this regard all reasonable combinations of embodiments described below are possible and form part of the invention.

According to claim 1 the medical implant device for attaching (or re-attaching) a flexible graft to a bone according to the invention, comprises:
- at least a first insert comprising or consisting of a synthetic osteoconductive and/or a synthetic osteoinductive material, and
- a flexible graft, wherein the flexible graft is connected to the at least one first insert, particularly prior to surgical implantation of the medical implant device.

In the sense of the present invention, a synthetic material is a material that is not taken from a human or animal body. Particularly, a synthetic osteoconductive and/or osteoinductive material is an artificially produced, i.e. man-made, material (e.g. by means of injection molding etc.)

It is to be noted, that the first insert alone (without a flexible graft) forms an aspect of the present invention, and may therefore be claimed alone. All features described herein relating to the (first) insert may be used to further characterize such an insert (without flexible graft) according to the invention.

According to a preferred aspect of the present invention, the first insert (and particularly further inserts) consist of or comprise said synthetic osteoconductive and/or osteoinductive material.

However, according to a further aspect of the present invention one may also use a first insert (and particularly a second insert or even more inserts, see below) that is an autografted and/or an allografted "bone block". Such a bone block (or bone blocks) may be combined with the further features described in herein, particularly in the claims.

Particularly, the present invention is related to a device and a surgical technique for soft tissue reconstruction, with particular application to anterior cruciate ligament (ACL)

reconstruction. Particularly, the disclosed approach allows one to utilize advantages of the well-known "bone-tendon-bone" (BTB) grafting technique when using graft materials that do not feature bone-like components, for instance the widely employed "hamstring" tendon autograft technique. The medical implant device and method (e.g. for ACL reconstruction) proposed herein are thus particularly designed to functionally augment standard soft-tissue grafts (e.g. hamstring autograft) with the incorporation of one or two e.g. osteoconductive and/or osteoinductive inserts (e.g. synthetic bone blocks made e.g. from porous tricalcium phosphate (TCP), hydroxyapatite, calcium sulphate, and/or calcium silicate, see also below). Particularly, a preferred embodiment also features caps (also denoted as "joint-space-protection-caps" which are fabricated e.g. out of polyether ether ketone [PEEK], or polylactide acid [PLA], or poly(lactic-co-glycolic acid) [PLGA], or polycaprolacton [PCL]) that particularly seal the osteoconductive/osteoinductive (first and/or second) insert from the joint space. These caps may also be configured to provide mechanical stability. Exemplary parameters of design for each part (osteoconductive/osteoinductive inserts, caps) are stated herein. Methods for graft preparation and surgical implantation relating to further aspects of the present invention, as well as validated prototype manufacturing processes are also described. Further, examples of the present invention have been tested for functional efficacy (e.g. pull-out strength) which is also described below.

In other words, particularly, the device according to the invention allows to effectively convert less painful grafting techniques such as the "hamstring autograft" into a BTB-like grafting technique.

Thus, in particular, a strategy for ACL reconstruction according to the present invention is to profit from the relative advantages of these two established grafting techniques. Particularly, the main idea is to apply one or several synthetic "bone-like" blocks in the form of a first and/or a second insert (e.g. comprising TCP) to a prepared ligamentous flexible graft (e.g. a hamstring autograft), achieving a configuration similar to bony blocks and ligament that characterize the BTB-graft. Because of excellent osteoinductive activity, TCP is particularly used as material comprised by the first and/or second insert as a preferred embodiment of the device according to the invention, especially as this material has been widely adopted for filling bone defects in the clinics.

Particularly, the TCP inserts disclosed herein are designed to provide sufficient contact surface of graft to bone or synthetic bone such as to induce host bone cells ingrowth into TCP scaffold and "heal" the scaffold rapidly and firmly within the host bone. Further, particularly, device components are preferably employed that avoid or minimize the possibility of damage to the osteoinductive/osteoconductive elements, and to minimize contact of the osteoconductive material with tissues in the joint space during surgery or postoperatively. Particularly, in a preferred embodiment of the present invention, the (e.g. TCP) inserts (also denoted blocks) are sealed with an e.g. degradable or biodegradable (e.g. PCL, PLA, PLGA, or similar (bio)degradable polymers that have been additionally formulated to be osteoconductive, e.g. manufactured in combination with TCP or HA) or non-degradable (e.g. PEEK) cap. These materials have been used within ligament fixation elements for years, given their good biomechanical properties and biocompatibility.

Particularly, in the sense of the present invention, a biocompatible material is a material that is able to be in contact with a living system, particularly a human, without producing an adverse effect. Further, particularly, in the sense of the present invention a degradable material is a material that chemically and/or mechanically degrades in the human or animal body over time (e.g. weeks, months, years). This can occur by various mechanisms depending on the material. Particularly, when the degradation is due to biological activity, e.g. a response from living matter provoked by the material, the degradation is also denoted as biodegradation.

Particularly, the osteoinductive/osteoconductive inserts (e.g. TCP) are combined with capping/sealing elements (e.g. PLA caps), and then these assemblies are being further combined with a flexible graft material (e.g. a hamstring autograft) to create a "bone-ligament-bone"-like configuration that promotes rapid biological attachment, with expected improvements in post-operative secondary stability compared to a hamstring autograft, while avoiding donor site pain associated with bony-block graft extraction at the patella and tibia. Particularly, by combination of this device with further (external) fixation means (e.g. endobuttons, interference screw etc.), both initial and long-term stability will be finally achieved.

To summarize, the present invention relates to a medical implant device, to a method for pre-implantation combination of the inserts and the flexible graft, as well as to the associated surgical techniques for implantation, and manufacturing techniques for producing the medical device according to the invention. Particularly, the medical implant device according to the invention can be used for anchoring a flexible (e.g. ligamentious) graft.

In the sense of the present invention, an osteoconductive material is a material that is designed to serve as a scaffold or guide for the reparative growth of bone tissue. Osteoblasts from the margin of the bone bore hole utilize such a material as a framework upon which to appropriately spread, migrate, proliferate, and ultimately generate new bone. In this sense an osteoconductive material may be regarded as a bone compatible material.

Further, an osteoinductive material is a material that is designed to stimulate osteoprogenitor cells to preferentially differentiate into osteoblasts that then begin new bone formation. An example for such osteoinductive cell mediators are bone morphogenetic proteins (BMPs), and tricalcium phosphate bearing biomaterials. Thus, an insert that is osteoconductive and osteoinductive will not only serve as a scaffold for currently existing osteoblasts but will also trigger the formation of new osteoblasts, and thus allows for faster integration of the insert into the bone.

Further, according to an embodiment of the medical implant device according to the invention, the medical implant device further comprises a second insert comprising an osteoconductive and/or osteoinductive material (particularly like the first insert, the second insert may consist of such a material). Particularly, the flexible graft comprises a first (e.g. proximal) end region and an opposing second (e.g. distal) end region. Particularly, the first insert is connected to the first end region, wherein the second insert is connected to the second end region, so as to achieve a bone-ligament-bone-like graft configuration, where the flexible graft is anchored via the inserts in a bone, respectively, such that the flexible graft extends between said bones (e.g. like in an ACL reconstruction).

Further, according to an embodiment of the medical implant device according to the invention, the first insert extends along a first axis, wherein the first insert is designed to be inserted into a bore hole of an associated bone in an insertion direction aligned with the first axis. Herein, a bore hole in the sense of the present invention is a hole in the bone that can be generated by boring or any other suitable technique (e.g. milling, chiselling etc.). Herein, a bore hole is also referred to as a bone tunnel.

Further, according to an embodiment of the medical implant device according to the invention, the second insert extends along a second axis, wherein the second insert is designed to be inserted into a bore hole of an associated bone in an insertion direction aligned with the second axis.

According to a further embodiment the medical implant device may also comprise a third insert that may comprise the individual features described herein for the first and the second insert. Preferably, the third insert is connected to the flexible graft such that two bundles (or sections) of the flexible graft extend from the third insert, which two bundles are then connected to the first and the second insert, e.g. in the manner described herein.

This three-insert-configuration of the medical implant according to the invention is ideal for the so called double bundle reconstruction technique. Here, the third insert is particularly configured to be inserted into a non-circular cylindrical bore hole Preferably, when only a first and a second insert are present, then, particularly, the first insert is configured to be inserted into a bore hole or bone tunnel of the femur, and the second insert into a bore hole or bone tunnel of the tibia. In case also a third insert is present, the third insert is configured to be inserted into a bore hole or bone tunnel of the femur while the first and the second insert are then configured to be inserted into a bore hole or bone tunnel of the tibia, respectively.

According to a preferred embodiment of the present invention the first, the second, and/or the third insert consists of or comprises one of the following substances: hydroxylapatite (HA), tricalcium phosphate (TCP), calcium sulphate, calcium silicate.

According to a preferred embodiment of the present invention, the first insert comprises a first region forming a first face side of the first insert, and an adjacent second region forming a second face side of the first insert, wherein the two face sides of the first insert face away from each other.

Further, according to a preferred embodiment of the present invention, the second insert comprises a first region forming a first face side of the second insert and an adjacent second region forming a second face side of the second insert, wherein the two face sides of the second insert face away from each other, Further, according to a preferred embodiment of the present invention, the first insert or the first region of the first insert and/or the second insert or the first region of the second insert consists of or comprises one of the following substances:

- a polymer, particularly a biocompatible polymer, wherein particularly this polymer is one of: degradable, particularly biodegradable, or non-degradable;
- a copolymer, particularly a biocompatible copolymer, wherein particularly this copolymer is one of: degradable, particularly biodegradable, or non-degradable;
- polyactic acid (PLA);
- poly(lactic-co-glycolic acid) [PLGA];
- polyglutamic acid (PGA);
- poly-ε-caprolactone (PCL);
- polyhydroxyalkanoate (PHA);
- polyether ether ketone (PEEK);
- a biocompatible derivative related to at least one of the above stated substances;
- a titanium alloy;
- a stainless steel;
- a composite of a polymer, particularly biocompatible polymer, and a bioceramics;
- a composite comprising PLA and TCP, wherein the PLA content preferably lies in the range from 30 wt % to 100 wt %, and wherein the rest is TCP (i.e. the TCP content lies in the corresponding range from 0 wt % to 70 wt %); particularly, the content of PLA is 70 wt % and the content of TCP is 30 wt %; preferably, the content of PLA is 30 wt % and the content of TCP is 70 wt %;
- a composite comprising PLA and HA;
- a composite comprising PCL and TCP;
- a composite comprising PCL and HA.

Particularly, in the sense of the present invention, a bioceramics or bioceramics material is ceramic material that is biocompatible. Particularly, as already described above, biocompatible means that the material is able to be in contact with a living system, e.g. a human, without producing an adverse effect (e.g. as defined in "Terminology for biorelated polymers and applications (IUPAC Recommendations 2012)", Pure Appl. Chem., Vol. 84, No. 2, pp. 377-410, 2012).

Further, according to an embodiment of the medical implant device according to the invention, the second region of the first and/or the second insert (or the entire first and/or second insert) consists of or comprises one of the following substances:

- an osteoconductive and/or osteoinductive bioceramics,
- hydroxylapatite (HA, $Ca_{10}(PO_4)_6(OH)_2$),
- tricalcium phosphate (TCP, $Ca_3(PO_4)_2$),
- calcium sulphate ($CaSO_4$),
- calcium silicate ($CaSiO_3$),
- or a derivative related to at least one of the above stated substances.

For manufacturing a first and/or second region of a first, of a second, or a of third insert, or for manufacturing a complete first, second, or third insert out of a bioceramic material, particularly TCP, a monomer like e.g. acrylamide and a cross linker like e.g. bisacrylamide can be used. However, these chemicals (monomer and cross linker) are preferably fully removed over a sintering process that is preferably used for hardening of the manufactured component.

However, it is also possible to make the above stated components out of a bioceramic material, particularly TCP, without such chemicals (e.g. monomer and cross linker), by only physically compressing the material (e.g. TCP powder) together and by sintering it.

Further, in case a composite component is manufactured comprising e.g. PLA and TCP (see above), no additional chemicals are used in particular, since here the PLA can act as a glue.

When the first and/or second insert (or even a further insert) comprises a first and a second region (e.g. as described above), the respective first region is preferably designed to be positioned nearer to the respective aperture of a bore hole or bone tunnel into which the respective insert is to be inserted or through which the graft extends from said insert to another insert (e.g. second or third insert). The respective second region is designed to be inserted (deeper) into the respective bore hole/bone tunnel for allowing the bone to grow into the second region which comprises said osteoconductive and/or osteoinductive material for this purpose.

The two regions (also denoted as zones) can either be separate regions that are e.g. assembled after individual manufacture, or can be integrally formed with one another, e.g. during a manufacturing process.

Further, according to an embodiment of the medical implant device according to the invention, the first region of the first insert of the medical implant device is formed as a cap connected to a face side of an insert body of the first insert, which insert body forms said second region.

Further, according to an embodiment of the medical implant device according to the invention, the first region of the second insert of the medical implant device is formed as a cap connected to a face side of an insert body of the second insert, which insert body of the second insert forms said second region of the second insert.

Particularly, said face side of the insert body of the first insert and/or said face side of the insert body of the second insert extends perpendicular to the respective axis. Particularly, the cap of the first insert faces the insert body of the first insert (e.g. its face side) in the direction of the first axis. Further, particularly, the cap of the second insert faces the insert body of the second insert (e.g. its face side) in the direction of the second axis.

The respective cap can be connected to the associated insert body in different ways. The connection can be a positive-connection, a substance-to-substance bond, and/or a force-fit connection.

Particularly, the cap or first region of the first insert is designed to separate the osteoconductive/osteoinductive insert body or second region of the first insert from direct contact with biofluids or tissues outside said bore hole or bone tunnel of the associated bone into which the first insert is to be inserted. Likewise, particularly, the cap or first region of the second insert is designed to separate the osteoconductive/osteoinductive insert body or second region of the second insert from direct contact with biofluids or tissues outside a bore hole or bone tunnel of the associated (e.g. further) bone into which the second insert is to be inserted (so that the graft extends between the two bones). This holds also for a possible third insert described above.

Further, according to an embodiment of the medical implant device according to the invention, the cap or first region of the first insert is designed to provide a resistance to a movement of the first insert counter to its insertion direction when the first insert is inserted into its associated bore hole.

Further, according to an embodiment of the medical implant device according to the invention, the cap or first region of the second insert is designed to provide a resistance to a movement of the second insert counter to its insertion direction when the second insert is inserted into its associated bore hole. This also applies to a possible third insert described above.

Particularly, for providing such a resistance, the cap or first region of the first insert comprises flexible protrusions which press against or engage with the associated bone when the cap or first region of the first insert is inserted into the bore hole of the associated bone.

Particularly, the cap or first region of the first insert comprises one of the following for providing said resistance, particularly a stepwise fixation in the bore-hole: barbs, circumferential rills, or similar structures to achieve a stepwise fixation.

Further, the cap or first region of the first insert may comprise at least to pins or wings protruding from the cap for providing said resistance (such pins or wings can be formed out of a plastic or a metal).

Additionally, the cap or first region of the first insert can be treated with any kind of surface treatment (tripods, a porous surface, a structured surface) to allow bony ingrowth.

The cap or first region of the second insert (as well as particularly the first region or cap of the third insert) may comprise the same means as the cap or first region of the first insert for providing resistance to a movement of the second insert counter to its insertion direction when the second insert is inserted into its associated bore hole.

Further, according to an embodiment of the medical implant device according to the invention, the medical implant device comprises a fixation means for fixing the medical implant device to a bone or to a plurality of bones, particularly to two bones, so that the first and/or second insert (and particularly also the third insert) can be re-positioned, particularly intraoperatively, along its respective axis in the respective bore hole.

According to a further embodiment of the medical implant device according to the present invention, the first insert comprises a main body (also denoted as core body) and a layer (e.g. a coating) attached to the main body. Further, also the second insert may comprises a main body (also denoted as core body) and a layer (e.g. a coating) attached to the main body. The layers or coatings may each form an outer layer of the respective (first or second insert).

Further, in an embodiment, the layer of the respective insert completely encloses the associated main body of the respective insert.

Furthermore, in an embodiment, the respective layer is formed out of or comprises one of the following substances:
 a polymer, particularly a biocompatible polymer, wherein particularly this polymer is one of: degradable, particularly biodegradable, or non-degradable;
 a copolymer, particularly a biocompatible copolymer, wherein particularly this copolymer is one of: degradable, particularly biodegradable, or non-degradable;
 a combination of different polymers.

Further, in an embodiment, the respective main body is formed out of or comprises one of the following substances:
 a bioceramics,
 an osteoconductive and/or osteoinductive bioceramics,
 hydroxylapatite,
 tricalcium phosphate,
 calcium sulphate,
 calcium silicate.

Further, according to an embodiment, the respective layer is designed to be degradable, particularly such that it degrades within a pre-defined period of time after implantation of the medical implant device according to the invention into the body of a patient. Particularly, said period of time is smaller than a year, particularly smaller than 6 months, particularly smaller than 3 months, particularly smaller than 2 months, particularly smaller than 1 month, particularly smaller than three weeks, particularly smaller than two weeks, particularly smaller than a week.

Due to this degradability, the main body can contact surrounding bone material of the patient after degradation of the surrounding layer so that bone can grow into the main body due to the osteoinductive or -conductive material comprised by the main body.

According to yet another embodiment (e.g. by way of a corresponding selection of the above stated substance) the respective layer is adapted to strengthen the associated main body.

According to yet another embodiment (e.g. by way of a corresponding selection of the above stated substance) the respective layer is adapted to seal off the associated main body so as to prevent release of said substance of the main body (particularly into a joint space)

Further, in all embodiments of the present invention, the flexible graft can be one of the following a: human tendon or ligament, a human autograft tendon or ligament, a human autograft hamstring tendon, particularly gracilus or semitendinosis, an allograft tendon or ligament, a xenograft tendon or ligament, or a synthetic tendon or ligament.

Further, according to an embodiment of the medical implant device according to the invention, the flexible graft is an elongated member that is folded at least once or a plurality of times so that the flexible graft comprises a plurality of (e.g. connected) strands (or sections) extending along each other, wherein particularly the flexible graft is folded at least two times so that the flexible graft comprises at least four strands extending along each other (i.e. along a longitudinal axis of the medical implant device), wherein particularly the flexible graft comprises merely or exactly four strands (e.g. due to folding it twice, wherein upon each folding the flexible graft is halved).

Particularly, in an embodiment where the medical implant device comprises two inserts, the flexible graft is folded two times so that it comprises four strands (see also below). Alternatively, in an embodiment where three inserts are present, the flexible graft is particularly also folded two times, wherein it is laid around the third insert so that two bundles extend from the third insert, wherein each bundle comprises two strands in particular.

Further, according to an embodiment of the medical implant device according to the invention, the first insert comprises a lateral surface extending along the first axis of the first insert, wherein the lateral surface of the first insert is designed to contact the associated bone when the first insert is inserted into the bore hole of the associated bone.

Further, according to an embodiment of the medical implant device according to the invention, also the second insert (and possibly also the third insert, see above) comprises a lateral surface extending along the second axis of the second insert, wherein the lateral surface of the second insert is designed to contact the associated bone when the second insert is inserted into the bore hole of the associated bone.

Further, according to an embodiment of the medical implant device according to the invention, the first insert comprises a first recess in the form of a furrow, which is formed in said lateral surface of the first insert and extends along the first axis, wherein at least one strand, particularly two strands, particularly four strands, is/are arranged in said first recess of the first insert.

Further, particularly, also the second insert comprises a first recess in the form of a furrow, which is formed in said lateral surface of the second insert and extends along the second axis, wherein at least one strand, particularly two strands, particularly four strands, is/are arranged in said first recess of the second insert.

Particularly, in this embodiment one may also say that the first and/or second insert comprises a C-shaped cross section perpendicular to the respective (first or second) axis.

Further, according to an alternative embodiment of the medical implant device according to the invention, the lateral surface of the first insert comprises a contact region extending along the first axis, which contact region of the first insert contacts at least one strand, and wherein particularly said contact region of the first insert comprises a convex bulge.

Further, particularly, also the lateral surface of the second insert comprises a contact region extending along the second axis, which contact region of the second insert contacts at least one strand, and wherein particularly said contact region of the second insert comprises a convex bulge.

Further, according to an alternative embodiment of the medical implant device according to the invention, the first insert comprises—besides said first recess (see above)—a second recess in the form of a furrow, which is formed in said lateral surface of the first insert and extends along the first axis, wherein at least one strand, particularly two strands, particularly three strands, is/are arranged in said second recess of the first insert, wherein said second recess of the first insert is formed on a side of the lateral surface of the first insert facing away from the first recess of the first insert.

Further, particularly, the second insert comprises—besides said first recess (see above)—a second recess in the form of a furrow, which is formed in said lateral surface of the second insert and extends along the second axis, wherein at least one strand, particularly two strands, particularly three strands, is/are arranged in said second recess of the second insert, wherein said second recess of the second insert is formed on a side of the lateral surface of the second insert facing away from the first recess of the second insert.

Particularly, one may also say that in this embodiment the first and/or second insert comprises an H-shaped cross section (or dented C-shaped cross section) perpendicular to the respective (first or second) axis.

Preferably, in this embodiment two strands may be arranged in each first recess and in each second recess, respectively. In this case the first and second recesses preferably have equal dimensions. Further, it is possible that only one strand is arranged in the first recesses while there are three strands arranged in the second recesses or vice versa.

Further, the first and/or the second insert may also comprise a third and particularly a fourth recess formed in the lateral surface of the respective insert. Here, all four recesses extend along the axis of the respective insert. Here, the recesses are preferably equidistantly spaced along the periphery of the respective insert. Particularly, in such a configuration the first and/or second insert may comprise some sort of a cross-shaped cross section perpendicular to the respective axis.

Further, according to an alternative embodiment of the medical implant device according to the invention, the first insert comprises a first recess in the form of a through-opening extending along the first axis, wherein all strands are arranged in said first recess of the first insert, and wherein the lateral surface of the first insert extends circumferentially around the strands and encloses the latter.

Further, particularly, also the second insert comprises a first recess in the form of a through-opening extending along the second axis, wherein all strands are arranged in said first recess of the second insert, and wherein the lateral surface of the second insert extends circumferentially around the strands and encloses the latter.

Particularly, in this embodiment one may also say that the first and/or second insert forms a shell, particularly a cylindrical shell extending along the respective (first or second) axis which encompasses the strands.

Further, according to an alternative embodiment of the medical implant device according to the invention, the lateral surface of the first insert contacts the strands, wherein particularly the lateral surface of the first insert is divided into four segments via four edges, wherein each edge extends along the first axis.

Further, particularly, also the lateral surface of the second insert contacts the strands, wherein particularly the lateral surface of the second insert is divided into four segments via four edges, wherein each edge of the second insert extends along the second axis.

Particularly, in this embodiment, the inserts are arranged between the strands wherein particularly the device is designed to contact the bone in the respective bore hole via the strands.

Further, generally, in all embodiments, the lateral surface of the first insert may comprise at least a region having a spherical curvature. Further, generally, in all embodiments, the lateral surface of the second insert may comprise at least a region having a spherical curvature.

Of course, the first and second insert may be shaped according to different embodiments described above. Any combination of the above described shapes/configurations is possible. Further, also the third insert may be shaped as described above with respect to the first or second insert. Also in case three inserts are present, the inserts may be shaped according to different embodiments described above. Any combination of the above described shapes/configurations is possible for the three inserts as well.

Further, according to an embodiment of the medical implant device according to the invention, the medical implant device comprises a first fixation means for fixing (or anchoring) the first insert to its associated bone, wherein the first fixation means comprises a first elongated flexible member that is looped around the first insert or second region/insert body of the first insert, and a second elongated flexible member that is connected to an end region of the first elongated flexible member of the first fixation means, wherein particularly the second elongated flexible member of the first fixation means is laid around the first elongated flexible member of the first fixation means, and wherein particularly the second elongated flexible member of the first fixation means is connected to a plate member of the first fixation means, which plate member is designed to butt against said associated bone when the first insert of the medical implant device is arranged in the bore hole of the associated bone, Particularly, according to an embodiment of the present invention, the first fixation means is used to add an additional functionality. For this, the first fixation means, e.g. the first or the second flexible member, may comprise an x-ray opaque marker that allows the implanted location of the medical implant device to be seen in an e.g. postoperative radiological control. As such a marker any suitable radiodense material can be used to hinder x-ray radiation from passing through the marker such that the marker can be seen on the corresponding radiographic image. The other fixation means (e.g. second and/or third fixation means) may also comprise such an x-ray opaque marker, which may for instance be comprised by one or all of the flexible members of these fixations means.

Particularly the, first elongated flexible member of the first fixation means is arranged in at least one furrow formed on the first insert.

Furthermore, particularly, the first elongated flexible member can be degradable, biodegradable or non-degradable. Particularly, the second elongated flexible member is non-degradable.

Further, particularly, the medical implant device comprises a second fixation means for fixing (or anchoring) the second insert to its associated bone.

Further, according to an embodiment of the medical implant device according to the invention, said second fixation means comprises a screw for fixing the second insert in the bore hole of its associated bone when the second insert is inserted in said bore hole Alternatively or in addition, the second fixation means may comprise a first elongated flexible member that is connected to a middle section of the flexible graft, wherein the second fixation means preferably comprises at least a second elongated flexible member that is connected to a first end section of the flexible graft, and preferably a third elongated flexible member that is connected to a second end section of the flexible graft, and wherein the second fixation means particularly comprises a plate member, which plate member is designed to butt against said associated bone when the second insert of the medical implant device is inserted into a bore hole of the associated bone. Preferably the plate member of the second fixation means is connected to the first, second and/or third flexible member of the second fixation means.

Further, according to an embodiment of the medical implant device according to the invention, the flexible graft is laid around the first insert, wherein the flexible graft is threaded through a loop formed by the second elongated flexible member of the first fixation means.

Particularly, said middle section of the flexible graft is arranged adjacent said first end section and adjacent said second end section of the flexible graft. Particularly, the middle section and the two end sections form the second end region of the folded flexible graft. On the other hand, when the flexible graft is not folded and extends along a straight line or longitudinal axis, flexible graft extends from said first end section via its middle section to its second end section.

Further, particularly, said middle section and said first and second end section of the flexible graft are connected to the second insert and/or contact the second insert, wherein particularly said middle section (having e.g. two strands) is arranged in the first recess of the second insert, and wherein particularly the first and the second end section (e.g. being each part of a strand) of the flexible graft are arranged in the second recess of the second insert.

This type of a (e.g. suture) connection enables the tensile force loading not only on the sutures (i.e. elongated flexible members) but also on the first insert. The proper mechanical stimulus on the first (and second) insert has a positive influence on the regeneration process.

Further, according to an embodiment of the medical implant device according to the invention, the flexible graft is connected to the first and/or second insert (e.g. either loosely or tightly) by means of flexible elements in the form of sutures, respectively.

Particularly, the largest tensile loads are carried via the flexible graft that runs through the second flexible member (e.g. suture) that is then secured by the first (external) fixation means (e.g. by its plate member).

Relatively smaller magnitude loads are transferred to the first insert via the looped first flexible member (e.g. suture), particularly just sufficient to hold it in the correct spatial location. This avoids insert damage (e.g. breakage), and also allows for some mechanical stimulus, which supports the tissue regeneration process. Particularly, this looped first flexible member also has the function of preventing the osteoconductive first insert from slipping into the joint space before it has healed (fused to the surrounding bone tunnel).

Further, according to an embodiment of the medical implant device according to the invention, the medical implant device may also comprise three inserts (see also above). Then, particularly, the flexible graft is folded once at a middle section which is laid around the first insert, wherein the flexible graft is threaded through said loop formed by the first elongated flexible member of the first fixation means.

Particularly, from said first insert two strands of the flexible graft extend toward the third insert (e.g. for insertion into the femur) and are laid around the third insert so that two strands of the graft extend from the third insert towards the second insert.

Here, one of the strands forms the first end section and the other strand the second end section of the graft. The two end sections are again connected to the second insert by means of flexible elements (e.g sutures) as in the case where only two inserts are present (cf. above).

At the third insert, namely at a central region of the (already folded) graft, the flexible graft is laid around the third insert, particularly such that two strands are arranged in a first recess of the third insert as well as in a second recess of the third insert, which second recess faces away from the first recess.

Here, the first and second insert may also each comprise a first and a second recess facing away from each other (as described above), wherein here each recess receives only one strand of the graft in particular.

Further, particularly, a third (external) fixation means may be provided for fixing the third insert in its associated bone tunnel, which third fixation means may also comprise a first and a second elongated flexible member, wherein the flexible graft may extend through the second elongated flexible member, which second member forms a loop and is laid around the first flexible member, which in turn is looped around the third insert or insert body/second region of the third insert. The second flexible member may be connected to a plate member of the third fixation means for anchoring the third insert with respect to its associated bone (e.g. femur). Other third fixation means (screws etc.) may also be used alternatively or in addition (see above).

Further, according to an embodiment of the medical implant device according to the invention, the first and/or the second insert (and particularly the third insert) is/are designed to be inserted into an associated bore hole of a bone with a loose-fit or a press-fit.

Generally, in all embodiments, the dimension of the first and/or second insert (and particularly third insert) may have a cross section that can be circumscribed by a periphery having preferably a diameter ranging between 2.0 mm and 15.0 mm, wherein particularly the first and/or second insert may have a length along the respective (first or second axis) within the range from 5.0 mm to 70.0 mm.

Particularly, the medical implant device is configured to be implanted through the tibia tunnel, or to be implanted through the medial side of the knee joint.

According to a further aspect of the present invention a method for producing an insert according to the invention (e.g. a first, second, and/or third insert), and particularly also a medical implant device according to the invention, is disclosed.

According thereto, a first female mold is provided and a fluid material forming an osteoconductive and/or osteoinductive material in a solid state is filled into the mold so as to cast a second region of the (e.g. first, second or third) insert (e.g. in the form of an insert body of the insert), wherein after hardening of the second region (e.g. by sintering) the first mold is removed from the second region and the second region is arranged with respect to a second female mold into which a material for a first region (e.g. in the form of a cap of the insert) was filled before, wherein the second region is arranged such with respect to the second mold that a face side of the second region (e.g. insert body) closes the second female mold and contacts the material filled into the second mold so that the first region is formed in a form-fitting manner with respect to the second region. Particularly, the first region is then hardened, e.g. by means of sintering.

This method is especially suited for mass production. However, it is of course also possible to produce the first and/or second region of the insert (e.g. cap and/or insert body) by milling them out of the respective material and by joining them thereafter as intended.

According to a further embodiment of said method according to the present invention, before the second region is arranged with respect to second mold (as described above), a first elongated flexible member is looped around the hardened second region (e.g. insert body) of the insert, and then the second region is arranged with respect to the second mold so that said face side of the second region (e.g. insert body) closes the second female mold and contacts the material filled into the second mold so that the first region is formed in a form-fitting manner with respect to the second region with the first elongated flexible member being enclosed between the first and the second region.

Further, particularly, a second elongated flexible member is laid around the first elongated flexible member so that the second elongated flexible member is fastened to the second region of the insert by means of the first flexible member. Particularly, the second elongated flexible member is connected to a plate member for fastening the medical implant device to a bone (the first and second flexible elongated member form a first fastening means together with the plate member, see also above).

Further, particularly, a flexible graft (which may be folded as described above) is laid around the first insert, wherein the flexible graft is threaded through a loop formed by the second elongated flexible member.

Further, particularly, the flexible graft is connected with an end region to at least a second insert (which may be manufactured as described above) such that the flexible graft extends between the first and the second insert.

Further, particularly, at least a first, particularly also a second, particularly also a third elongated flexible member forming part of a second fixation means are connected to said end region of the flexible graft.

Further, particularly, the first elongated flexible member forming part of the second fixation means is connected to a middle section of the flexible graft, and the second elongated flexible member forming part of said second fixation means is connected to a first end section of the flexible graft, and the third elongated flexible member forming part of said second fixation means is connected to a second end section of the flexible graft, wherein said end region of the flexible graft is formed by said middle section and said two end sections which are arranged adjacent to one another.

Further, particularly, said first, second, and/or third flexible elongated member of the second fixation means are connected to a plate member of the second fixation means for fastening the medical implant device to the bone.

Further, particularly, in case three inserts are used, after having formed or provided said three inserts (i.e. a first, a second and a third insert) as described above, a second elongated flexible member is laid around the first elongated flexible member so that the second elongated flexible member is fastened to the second region of the first insert by means of the first flexible member. Particularly, the second elongated flexible member is connected to a plate member for fastening the medical implant device to a bone (the first and second flexible elongated member form a first fastening means together with the plate member, see also above).

Further, particularly, a flexible graft (which may be folded as described above) is laid around the first insert, wherein the flexible graft is threaded through a loop formed by the second elongated flexible member.

Further, particularly, a third (external) fixation means is provided for fixing the third insert in its associated bone tunnel, which third fixation means comprises the first elongated flexible member that is looped around the third insert or insert body/second region of the third insert, and a second elongated flexible member, wherein the second flexible member is laid around the first flexible member of the third insert, and wherein the flexible graft is passed through a loop formed by the second elongated flexible member of the third fixation means. Particularly, the second flexible member is connected to a plate member of the third fixation means for anchoring the third insert with respect to its associated bone (e.g. femur). Other third fixation means (screws etc.) may also be used alternatively or in addition (see above).

Further, particularly, the graft being passed through the loop of the second flexible member of the third fixation means is laid around the third insert (e.g. as described above).

Further, particularly, the flexible graft is connected with an end region (e.g. with its first and its second end section) to a second insert such that the flexible graft extends from the first insert to the third insert and from the third insert to the second insert.

Further, particularly, at least a first, particularly also a second elongated flexible member forming part of a second fixation means are connected to said end region of the flexible graft, wherein particularly the first flexible member is connected to the first end section and the second flexible member is connected to the second end section of the graft.

Further, particularly, said first and/or second flexible elongated member of the second fixation means are connected to a plate member of the second fixation means for fastening the medical implant device to the bone.

Figure 2:
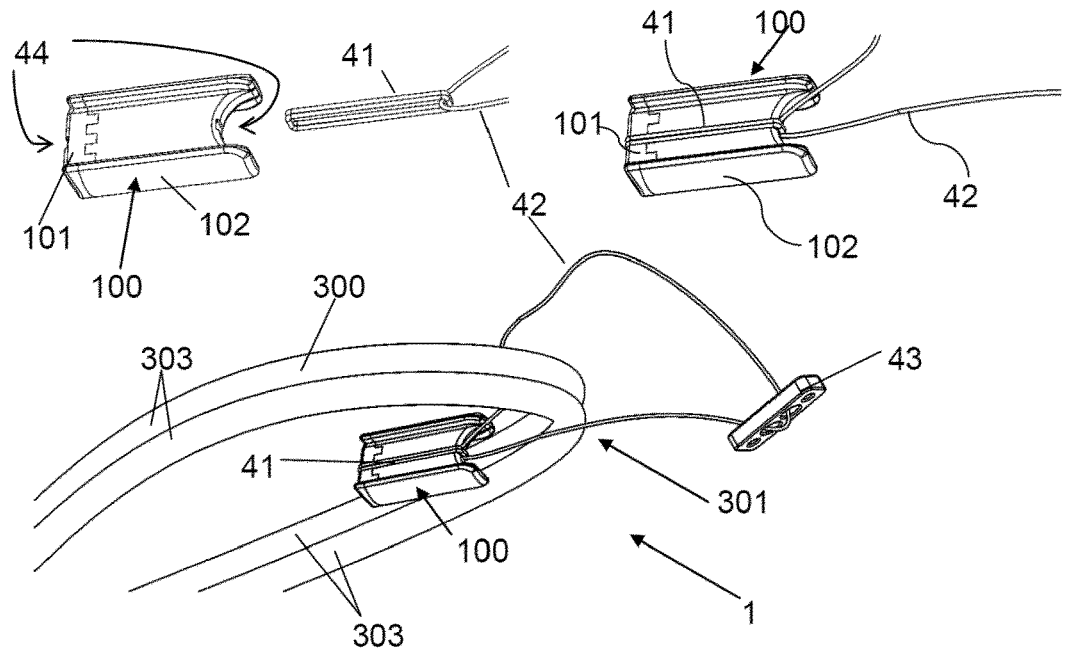

Further features and advantages of the invention shall be described by means of detailed descriptions of embodiments with reference to the Figures, wherein FIG. 1 shows a view of an embodiment according to the invention (left hand side) as well as a detail of the device according to the invention (right hand side), FIG. 2 shows further details of the embodiment shown in FIG. 1

Figure 3:
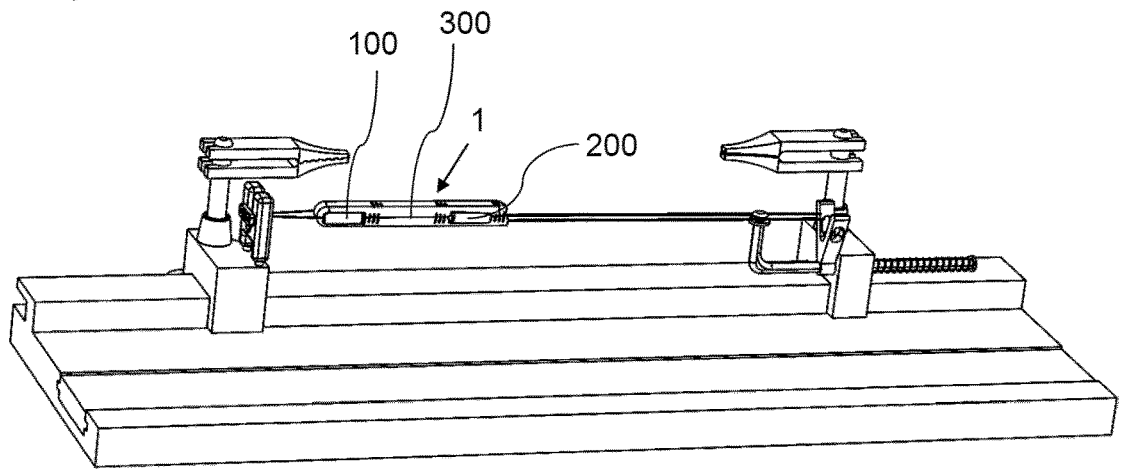
Figure 4:
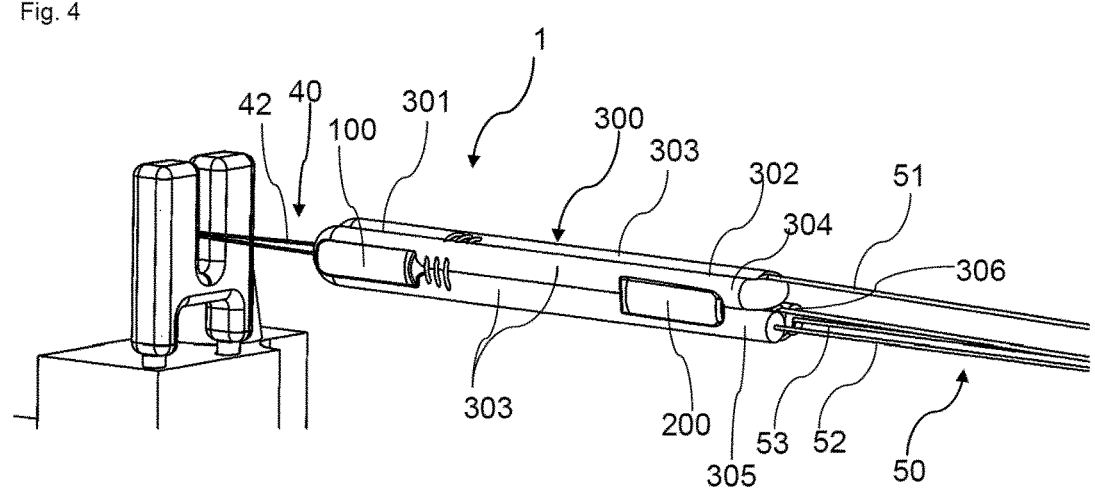
Figure 5:
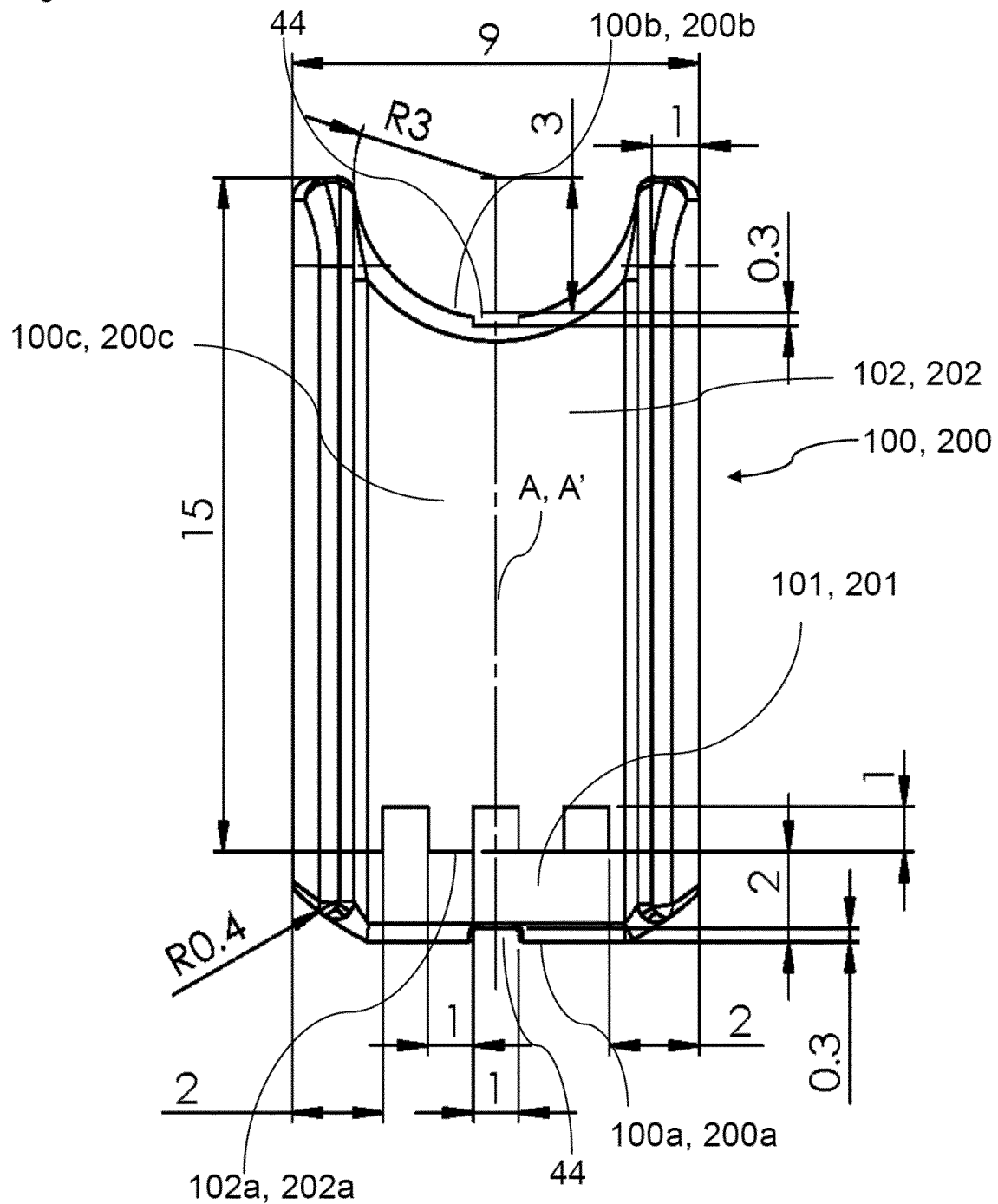
Figure 6:
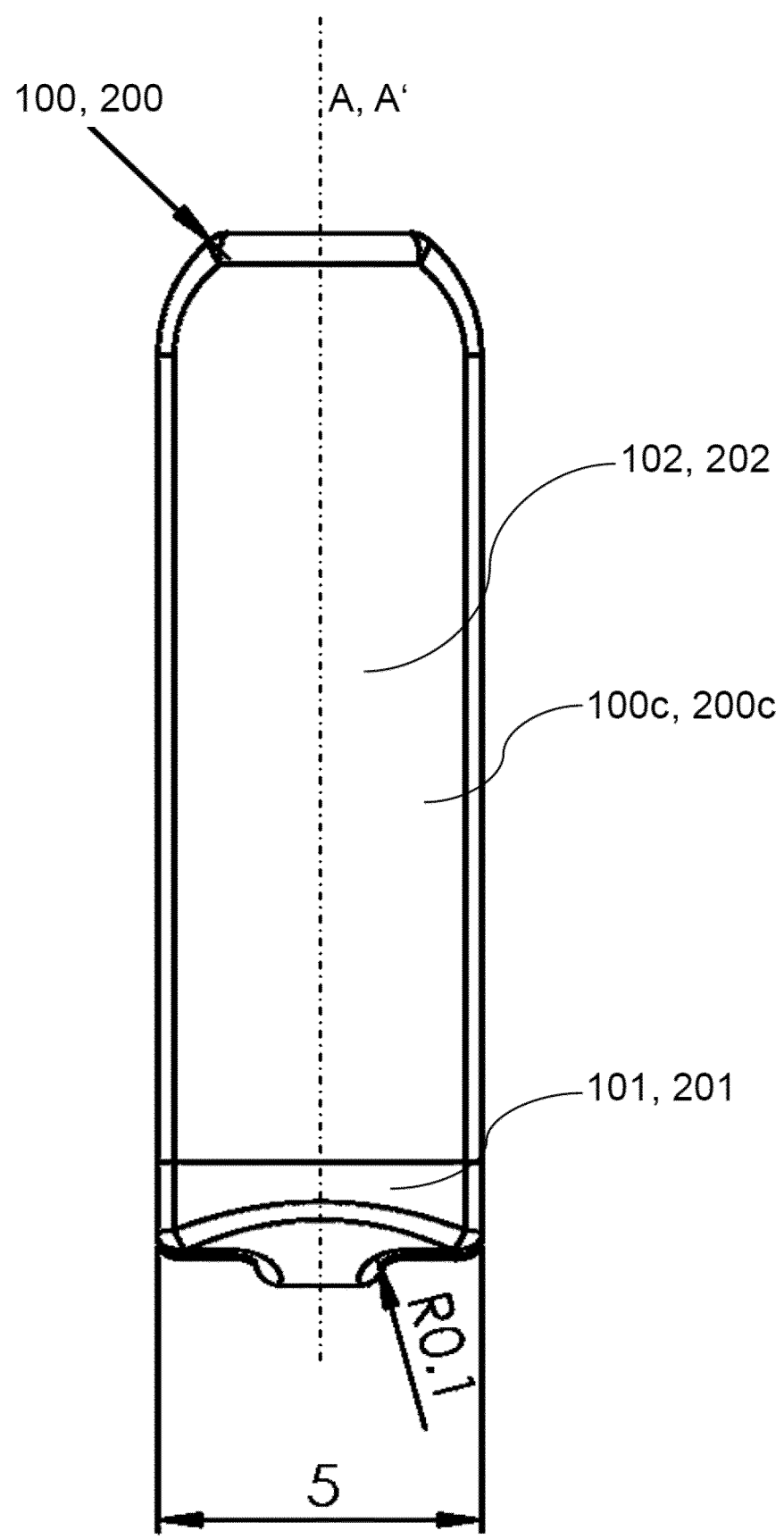
Figure 7:
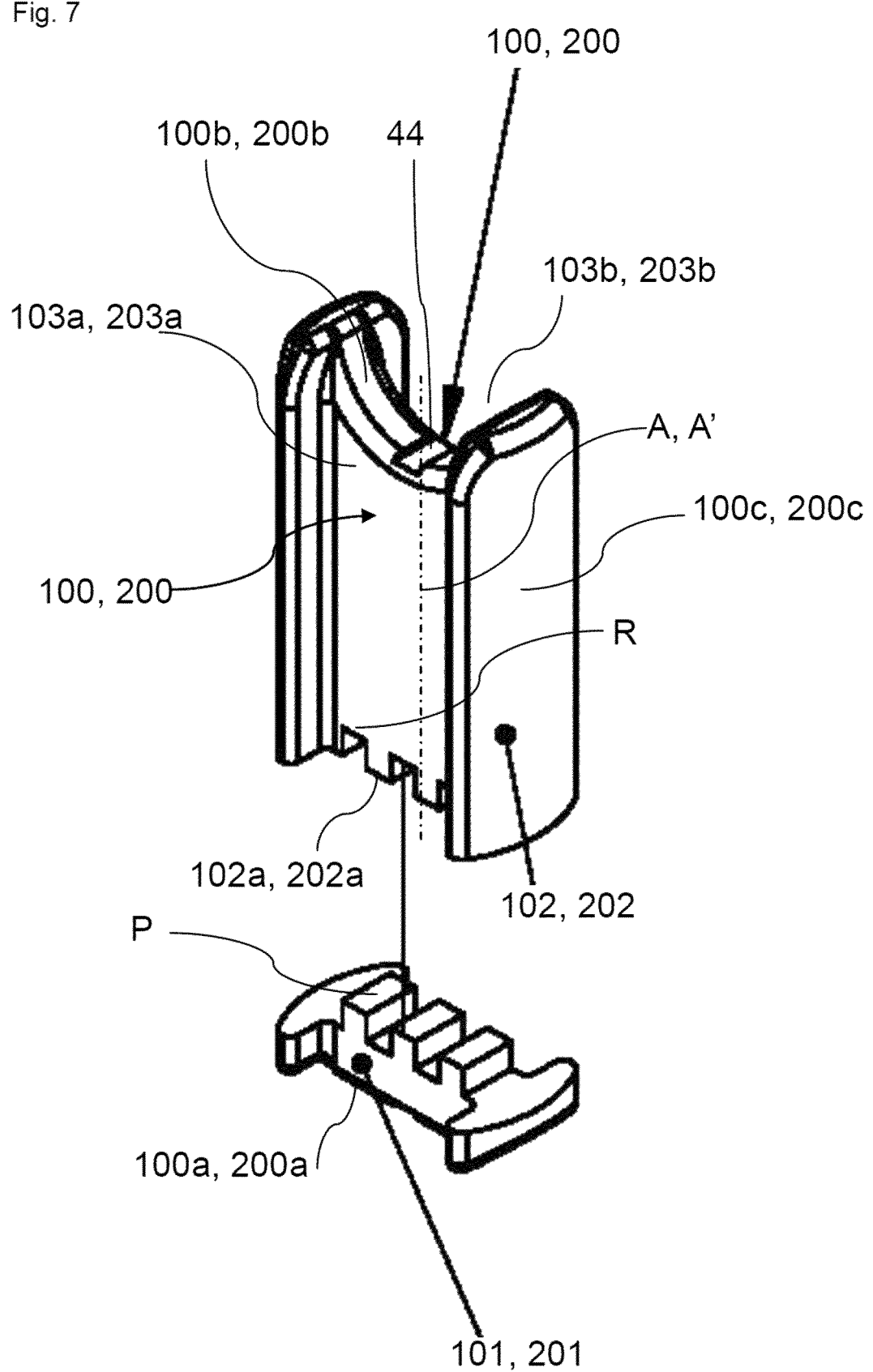
Figure 19:
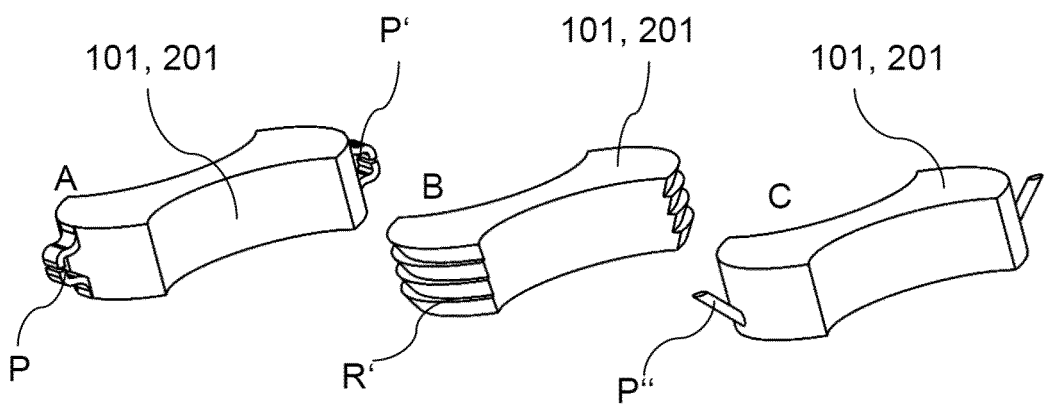
Figure 20:
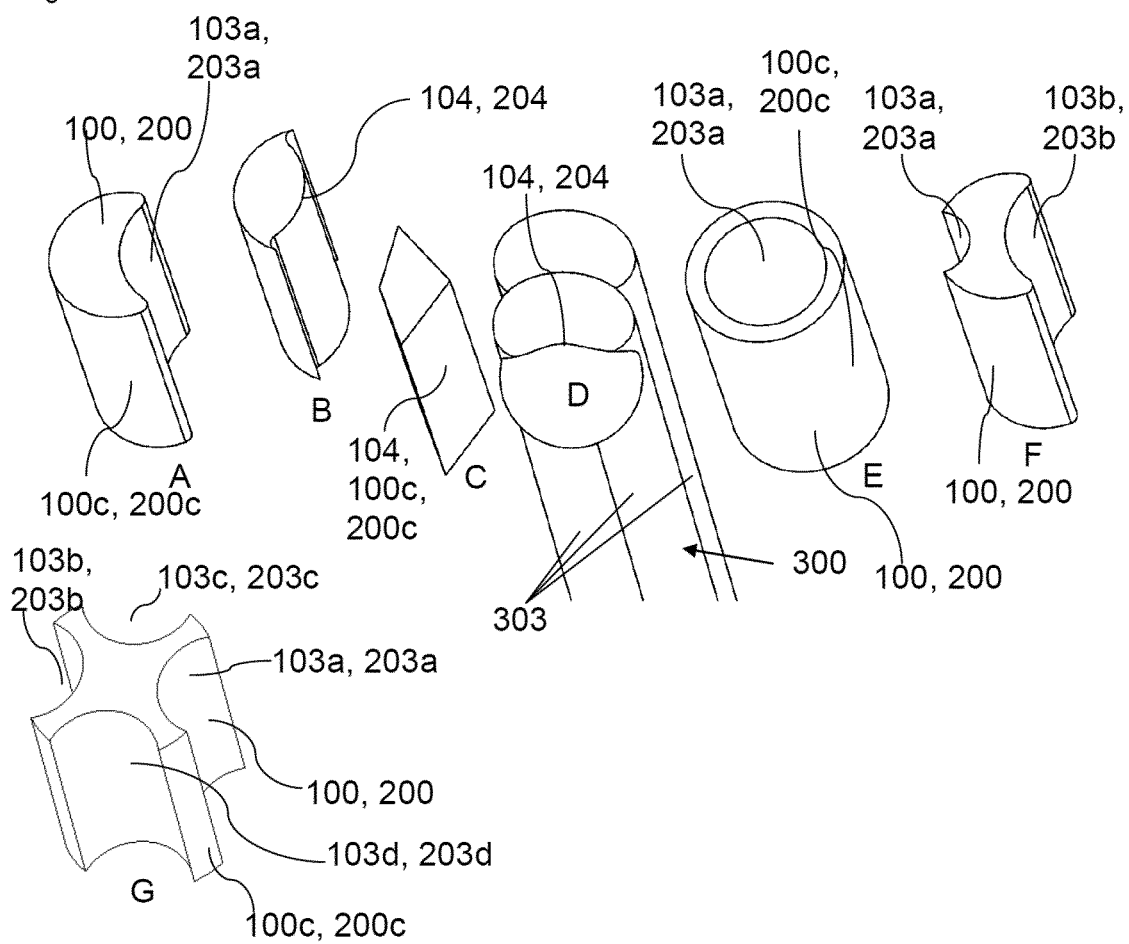
Figure 21:
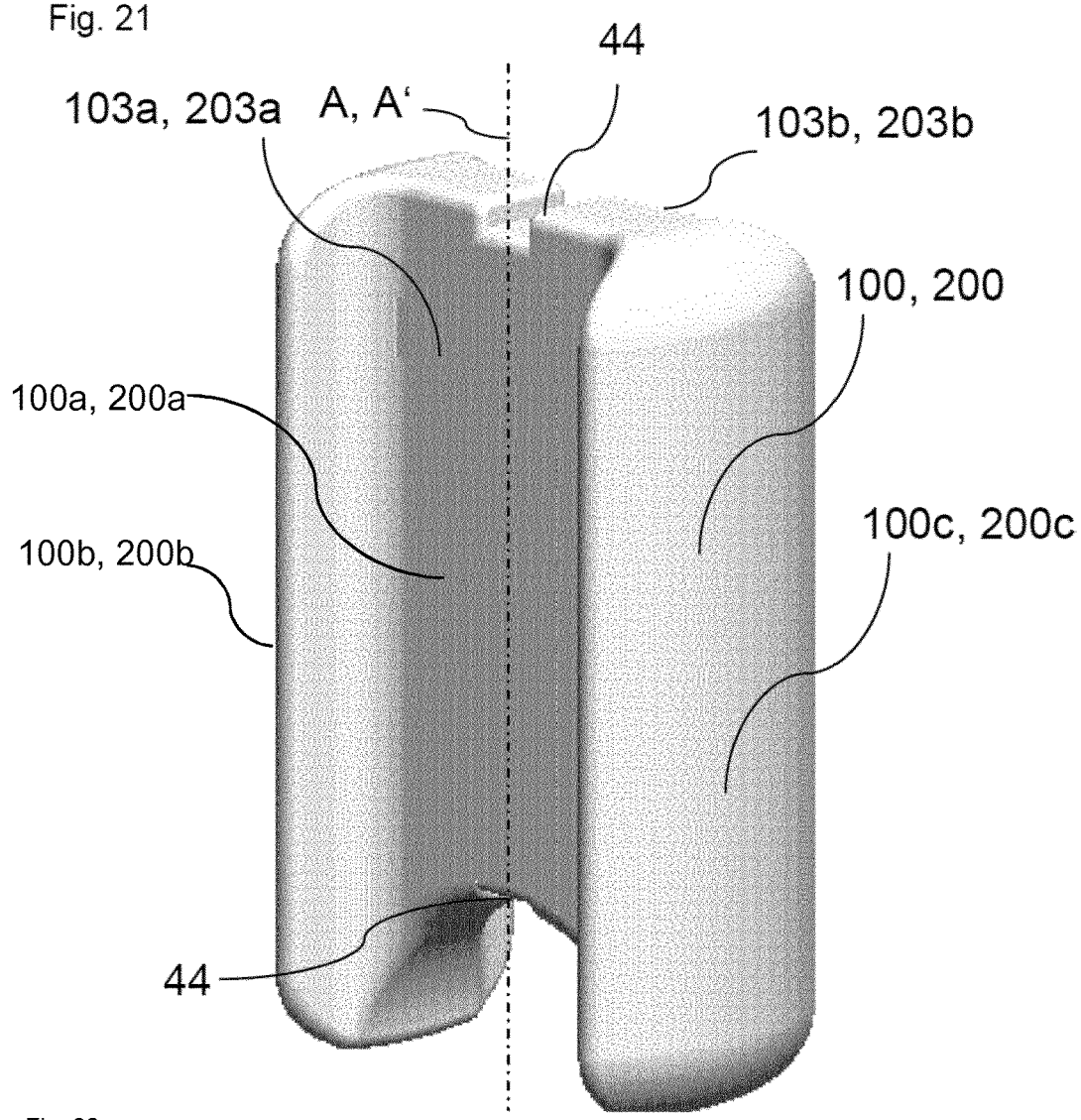
Figure 22:
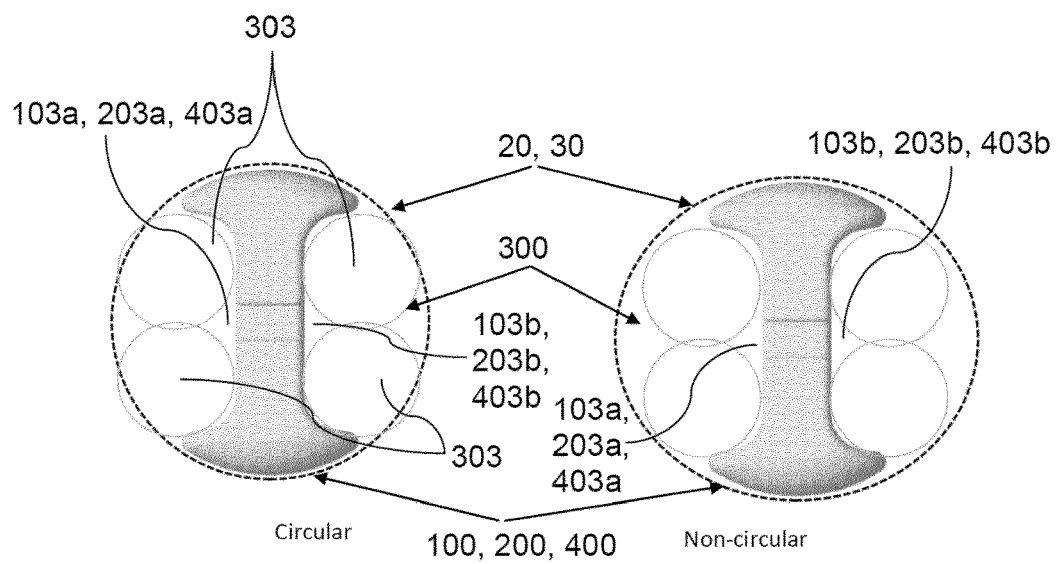
Figure 23:
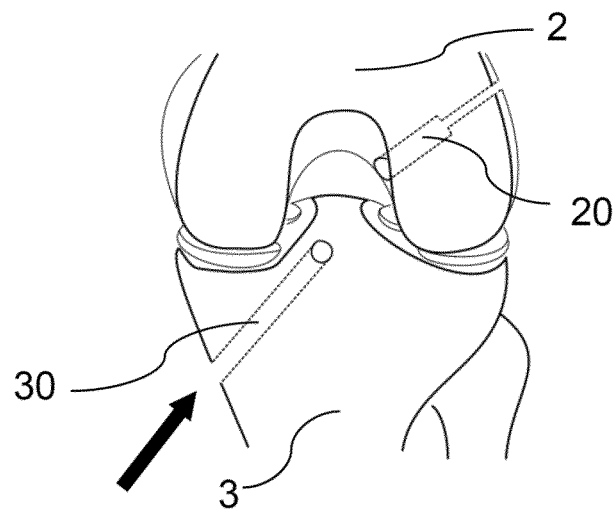
Figure 24:
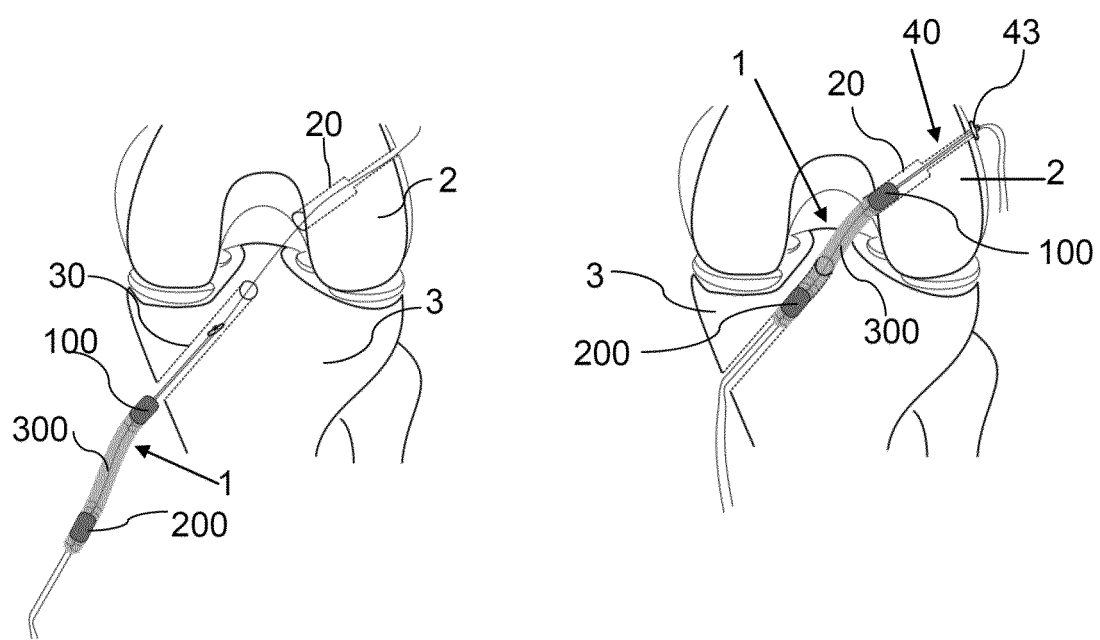
Figure 25:
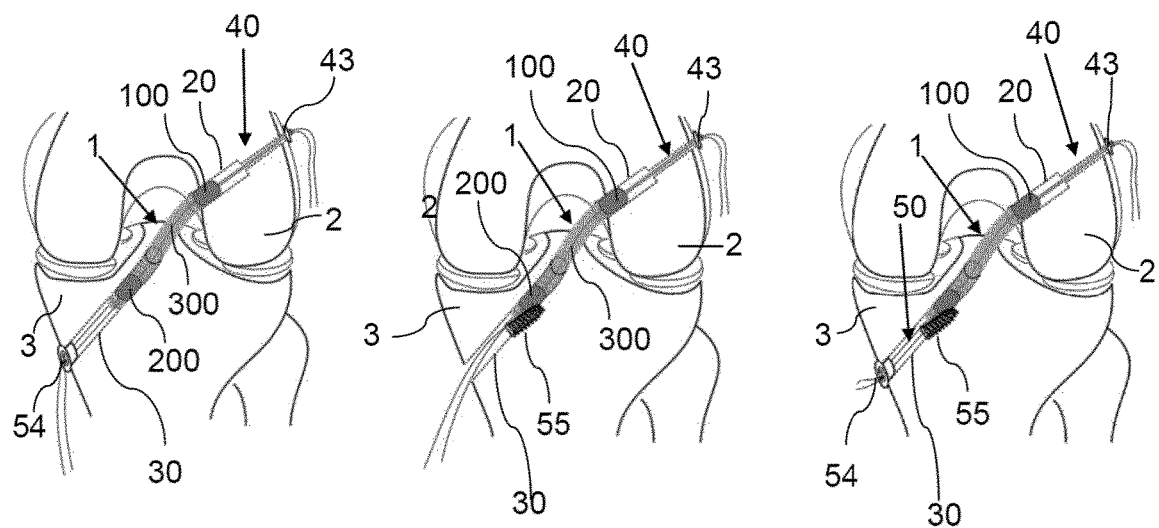
Figure 26:
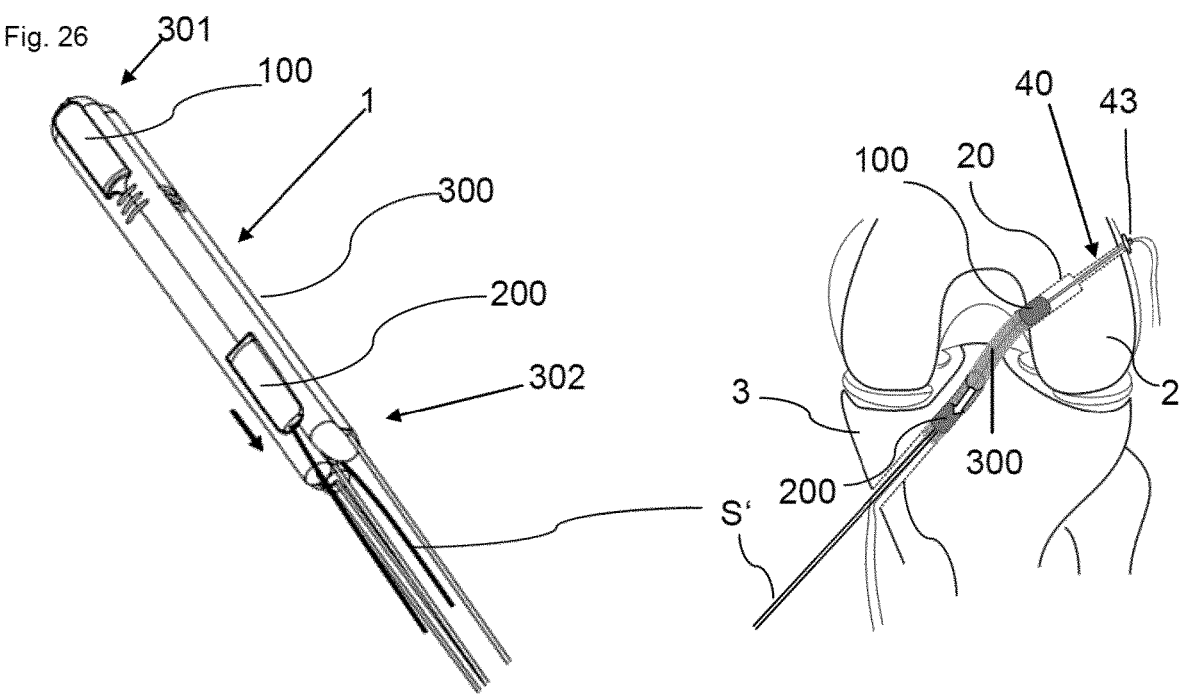
Figure 27:
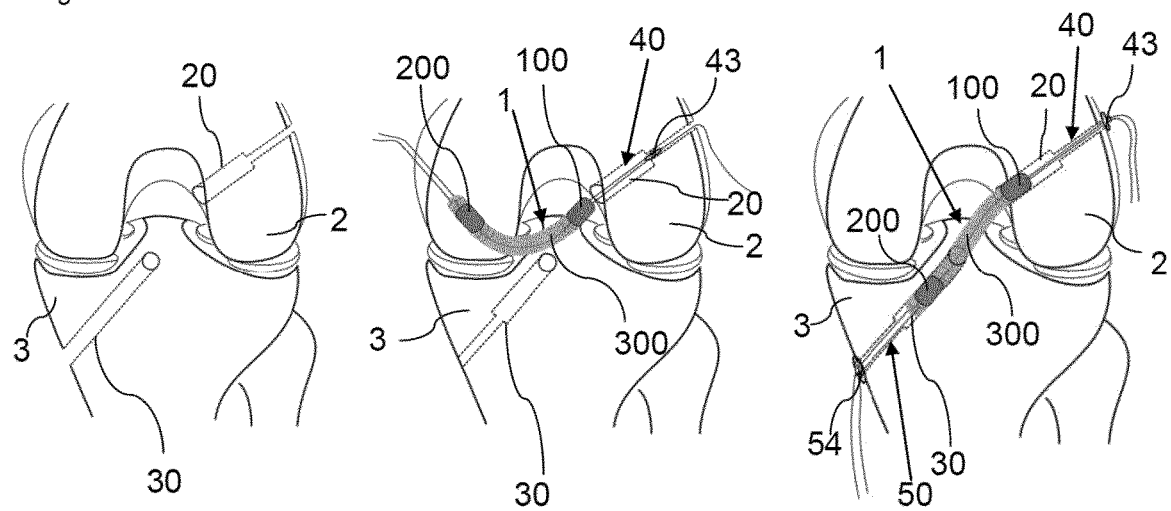
Figure 28:
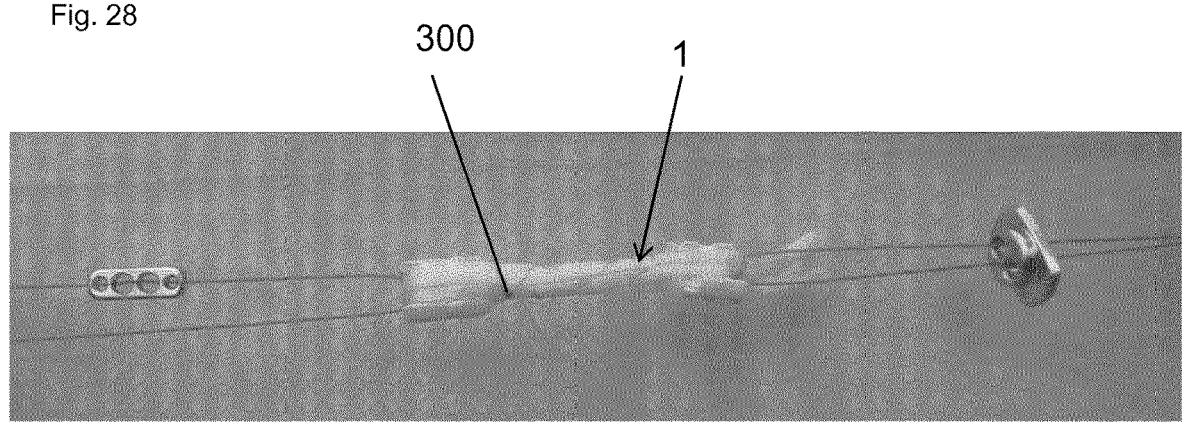
Figure 29:
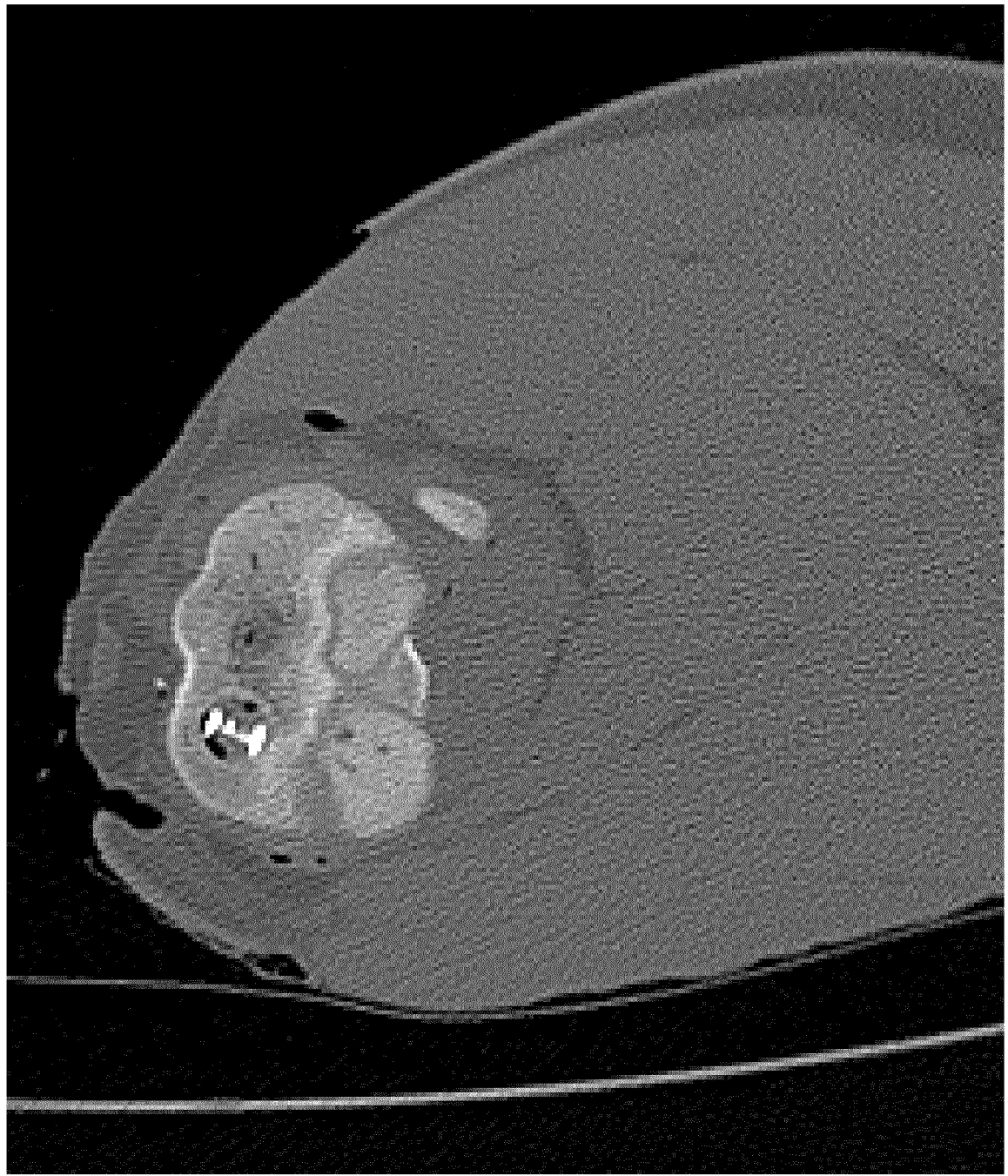
Figure 30:
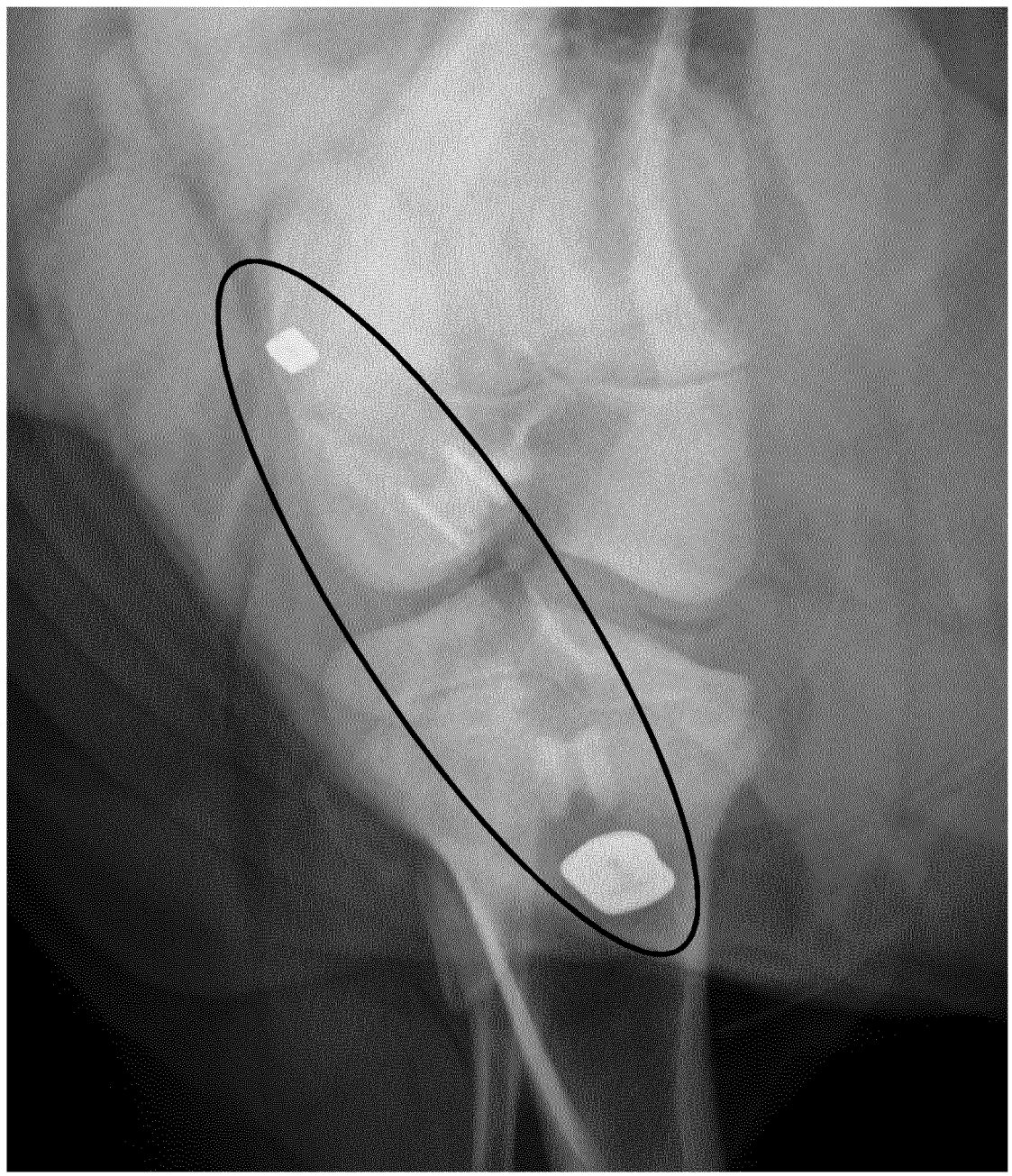

FIG. 3 shows a perspective view of a preparation board for generating a device according to the invention, which here comprises a quadrupled flexible graft (e.g. autograft), FIG. 4 shows a detail of FIG. 3, namely the quadrupled flexible draft and a first insert connected to the first insert by additional suturing, FIGS. 5 to 9 show different views of a first (or second) insert of a medical implant device according to an embodiment of the present invention, FIGS. 10 to 18 shows the production/assembly of a medical implant device according to the invention, FIG. 19 shows different embodiments of first (or second) caps of a medical implant device according to the present invention, FIG. 20 shows different embodiments of first (or second) insert of a medical implant device according to the present invention, FIG. 21 shows a perspective view of an embodiment of a first (or second) insert of a medical implant device according to the invention wherein the device does not comprise a first or second cap, but an integrally formed first (or second) insert, FIG. 22 shows that the bore hole or the first or second insert together with the flexible graft may have a circular cross section or a cross section that deviates from the circular contour (i.e. an elliptical cross section etc.), FIG. 23 shows a possible way of generating the two bore holes (e.g. for an ACL reconstruction) during surgery, FIG. 24 shows a possible way of arranging a medical implant device according to the invention in the bore holes of FIG. 23, FIG. 25 shows different ways of fixing the medical implant device shown in FIG. 24 to the bones, FIG. 26 shows a possibility of adjusting the axial position of the second insert in its bore hole, FIG. 27 shows an alternative way of arranging a medical implant device according to the invention in the two bore holes, FIG. 28 shows a further view of an example of the present invention, FIG. 29 shows a radiograph of an implanted medical implant device of the kind shown in FIG. 28, FIG. 30 shows a CT scan of an implanted medical device according to the invention after implantation, and FIG. 31 shows a so called double bundle configuration of a medical implant device according to the invention.

Particularly, the key subassembly of medical implant device 1 according to the invention is the first or second insert 100, 200 (particularly also a third insert 400, see below), which is also denoted as hybrid (first or second) insert in case the medical implant device 1 comprises a cap/first region 101 connected to an insert body/second region 102 of the first insert 100 (or a cap/first region 201 connected to an insert body/second region 202 of the second insert 200), which insert bodies 102, 202 are formed as an osteoconductive/osteoinductive bone block (e.g. comprising TCP), respectively, to promote bone ingrowth to the medical implant device 1 from the surrounding host bone tissue. The respective cap 101, 201 forms a sealing cap (e.g. out of a polymer or a metal) that protects the respective insert body 102, 202 from damage, seals the outer margins of the respective bore hole (also denoted as bone tunnel) 20, 30, and optionally features mechanical fixation elements that can provide mechanical resistance to axial movement of the inserts 100, 200 within the respective bone tunnel.

FIGS. 1 to 2, and 5 to 9 show a preferred embodiment of the present medical implant 1 according to the invention. The assembly of such a device 1 is shown for instance in FIGS. 11 to 18.

In this embodiment, the first and the second insert 100, 200 are made of two solid components 101, 102 as well as 201, 202, which are particularly conjoined during a molding process. Particularly, a tricalcium phosphate (TCP) first and second insert body 102, 202 and a smaller first and second (e.g. polymer) cap 101, 201 are used. Because of good biomechanical and biological properties both materials are commercially available products of ligament anchors used in clinics. Due to excellent osteoinductive capabilities, TCP scaffolds have been used as the artificial bone in clinics for many years. Particularly, an idea of the present invention is to enlace the flexible graft 300 (e.g. tendon autograft or silk ACL scaffold, etc.) onto a porous TCP scaffold 100, 200 and combine it with e.g. resistant non-degradable flexible elongated members 41, 42, 51, 52, 53 (e.g. reinforced sutures, e.g. Fiberwire) of first and second fixation devices 40, 50. As the bone cell gradually grows into the porous TCP scaffold 100, 200, the autograft (or silk scaffold) will be held by the TCP/Bone interface within the bone tunnel 20, 30. In the long-term, the TCP scaffold 100, 200 will be fully regenerated with the new born bone, and the tendon autograft (or silk ACL scaffold) will be attached onto the native bone tissue firmly. The biological fixation will be finally achieved. Due to the porous nature of the TCP part 102, 202, small pieces can break of during surgery or rehabilitation. To prevent those parts to get into the joint space, the TCP parts (i.e. the first and second insert 100, 200) are sealed with (e.g. polymer) caps 101, 201 (e.g. polylactic acid (PLA), or polycaprolactone (PCL), or polyetheretherketone (PEEK)). Besides TCP also other osteoinductive or osteoconductive materials may be used.

To provide initial stability and fixation of the medical implant device 1 using the first fixation means 40, the latter comprises two different elongated flexible members (e.g. forming sutures) 41, 42. Hereby, being a well-established method in ACL reconstruction, the looped flexible graft 300 is secured with a second flexible member 42 (e.g. a high resistant reinforced continuous suture loop, e.g. Fiberwire), forming a loop (which is also denoted as external fixation suture loop). This external second flexible member 42 in turn runs through a plate member 43 (e.g. a flappable button such as an endobutton), which seizes by tension on the outer side of the bore hole 20. Further, a first e.g. (bio)degradable (or non-degradable) flexible elongated member 41 (e.g. of the first fixation means (e.g. also in form of a suture, which is therefore also called the inner suture), is wrapped around the first insert 100, e.g. around the first cap 101 and the insert body 102 of the first insert 100 (the insert body 102 and the cap 101 form a so called hybrid insert), as well as around the second flexible elongated member 42. This provides additional security for exact positioning of the first insert 100 and prevents it from moving in the joint. To constrain the first flexible member 41 from lateral slippage, furrows 44 are countersinked at the top and bottom of the hybrid first insert 100, 200. I.e. one furrow 44 is arranged on the second face side 100b of the first insert 100, which second face side 100b faces away from the face side 102a of the insert body 102 to which the cap 101 of the first insert 100 is attached. The other furrow 44 is formed in the first face side 100a of the cap 101 or first insert 100 which first face side 100a faces away from said face side 102a of the insert body 102 of the first insert 100. The first fixation means 40 is for instance shown in FIG. 2. As already mentioned above, the first fixation means 40 (and also the other fixation means) may potentially be used to bring additional functionality by using it as a (at least partially) x-ray opaque marker that enables the implanted location of the implant device 1 to be seen in postoperative radiological control Preferably, as shown in FIGS. 3 and 4 in conjunction with FIGS. 11 to 19, the flexible graft 300 is threaded through a first elongated flexible member 51 of a second fixation means 50, which elongated flexible member 51 comprises a loop configuration. Then, the flexible graft 300 is folded at a middle section 304, where the first flexible member 51 of the second fixation means 50 is arranged, and a first and an opposing second end section 305, 306 of the flexible graft 300 are sutured S together by means of a flexible elongated member, such that a second elongated flexible member 52 extends from the first end section 305, and such that a third flexible elongated member 53 extends from the second end section 306 of the flexible graft.

Figure 14:
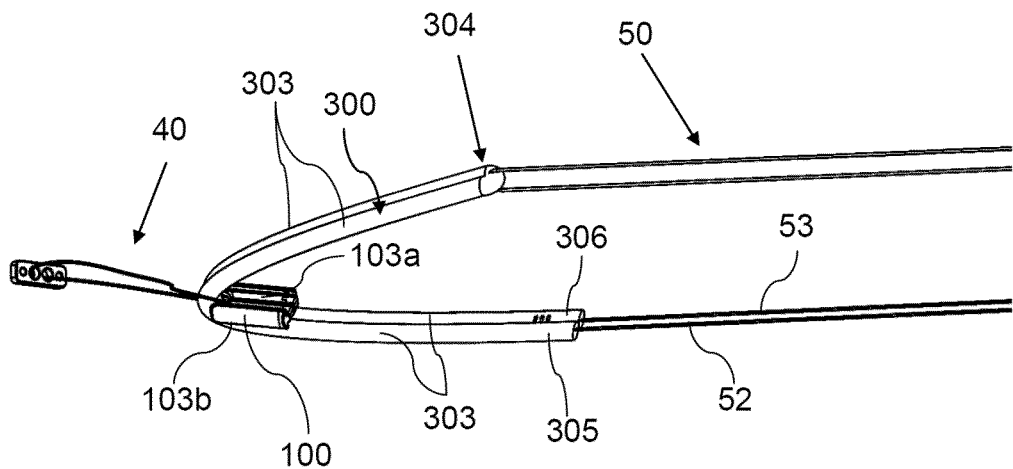
Figure 15:
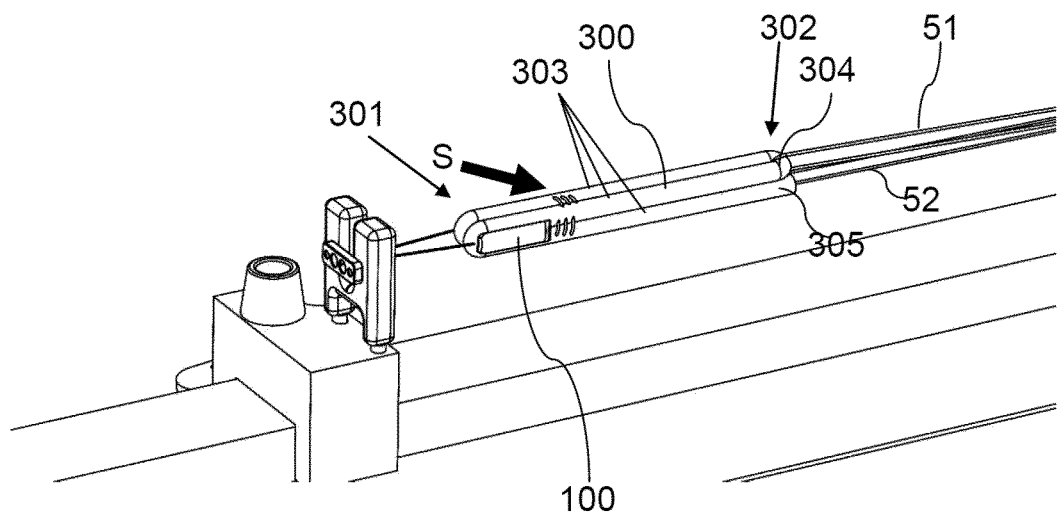
Figure 16:
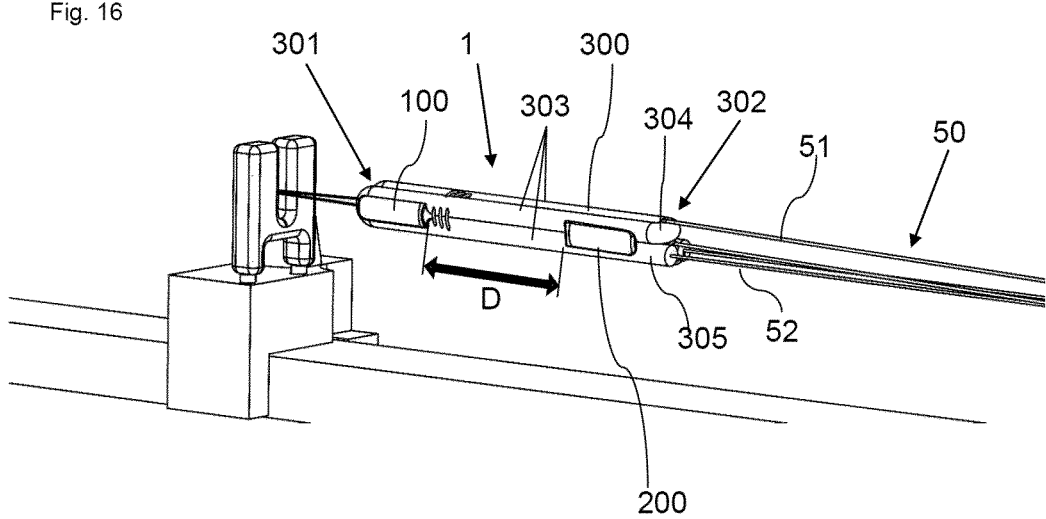
Figure 17:
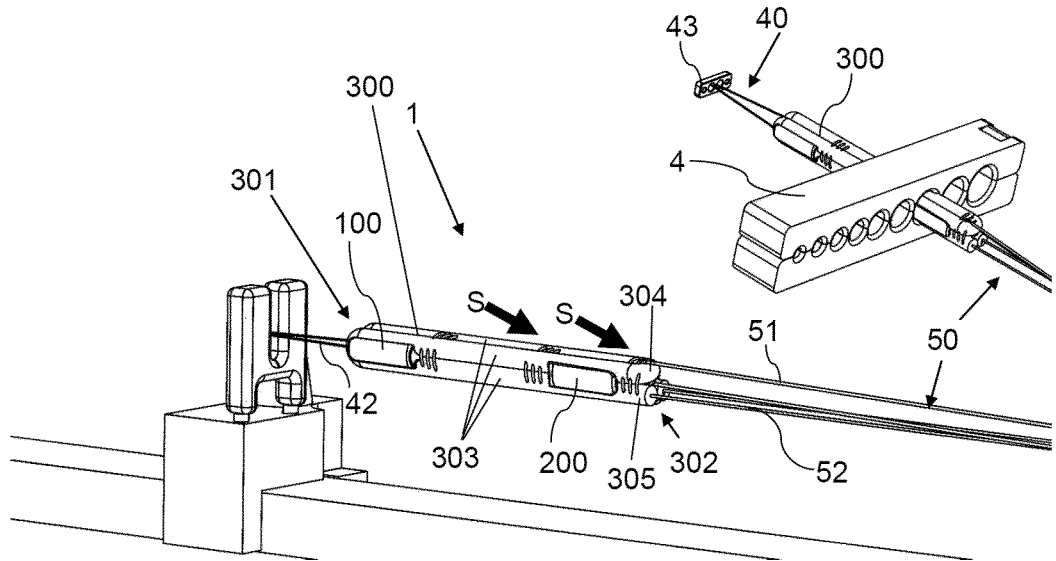
Figure 18:
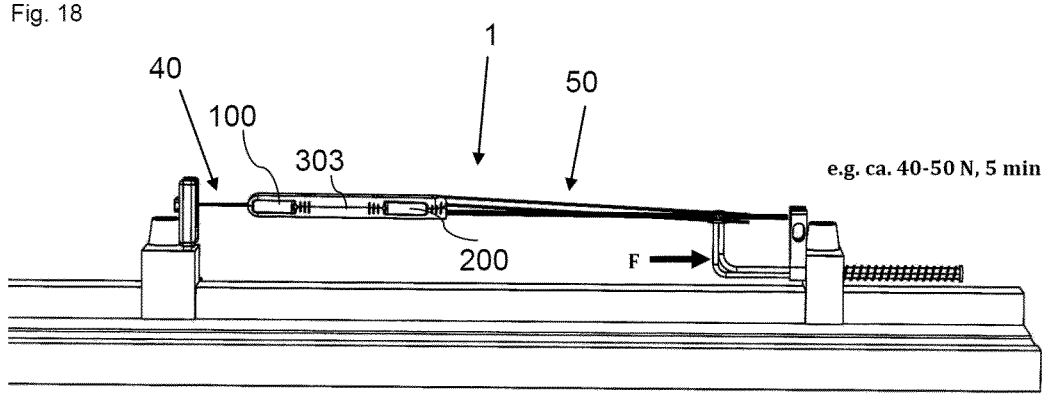

In a next step, as shown in FIG. 14 the flexible graft 300 is laid around the first insert 100 such that the flexible graft 300 is folded a second time. Here, two strands 303 of the now quadrupled graft 300 are arranged in a first recess 103a of the first insert 100, while two further strands 303 are arranged in a second recess 103b of the first insert 100 (see also FIG. 22). The strands 303 now get sutured together with a suture S just right behind the first (hybrid) insert 100 as shown in FIG. 15. Finally, a second (hybrid) insert 200 is mounted mirror wise at a pre-defined distance D (along the flexible graft 300) with respect to the first insert 100 (cf. FIG. 16) with another pair of sutures S placed on both sides of the second insert 200, wherein these sutures S hold the four strands 303 together, respectively, which is shown in FIG. 17. Here, FIG. 17 also shows a device 4 for measuring the outer diameter of the flexible graft 300/device 1. The first and the second insert 100, 200 can have the same shape. However, also different embodiments of the first and second insert 100, 200 may be combined.

In detail, as shown in FIGS. 5 to 9 the first insert 100 extends along a first axis A (in the following, only the first insert 100 is described for simplicity; the second insert 200 extending along a second axis A' as well as its insert body 202 and cap 201 can be configured according to the first insert 100; likewise also the third insert 400 can be designed according to the first insert 100). Particularly, the first insert 100 is designed to be inserted into a bore hole 20 of an associated bone 2 (e.g. the femur) in an insertion direction aligned with the first axis A (cf. also FIG. 1). Further, the cap 101 is connected to a face side 102a of the insert body 102 of the first insert 100 in a form-fitting manner, wherein the cap 101 may comprise protrusions P extending parallel to the first axis A, which protrusions P engage with associated recesses R of the insert body 102 of the first insert 100 in a form-fitting manner (cf. FIG. 7).

Particularly, the cap 101 of the first insert 100 is designed to provide a resistance to a movement of the first insert 100 counter to its insertion direction when the first insert 100 is inserted into the bore hole 2 of its associated bone 20, wherein particularly the cap 101 of the first insert 100 can assume also the shapes shown in FIG. 19 A to C.

According to FIG. 19A the cap 101 may comprise flexible protrusions P' which press against or engage with the associated bone 20 when the cap 101 is inserted into the bore hole 2 of the associated bone 20.

Further according to FIG. 19B, the cap 101 may comprise circumferential rills R' for providing said resistance, particularly a stepwise fixation in the bore-hole.

Further, according to FIG. 19C, the cap 101 may comprise at least two pins P'' protruding in a radial direction, wherein particularly these pins P'' protrude under an acute angle from a cap body of the cap 101 so that they can deform towards said body when inserting the first insert 100, e.g. its insert body 102 together with the cap 101 connected thereto, into the associated bore hole 20, but provide resistance when trying to pull the first insert 100/cap 101 out in the opposite direction.

Figure 8:
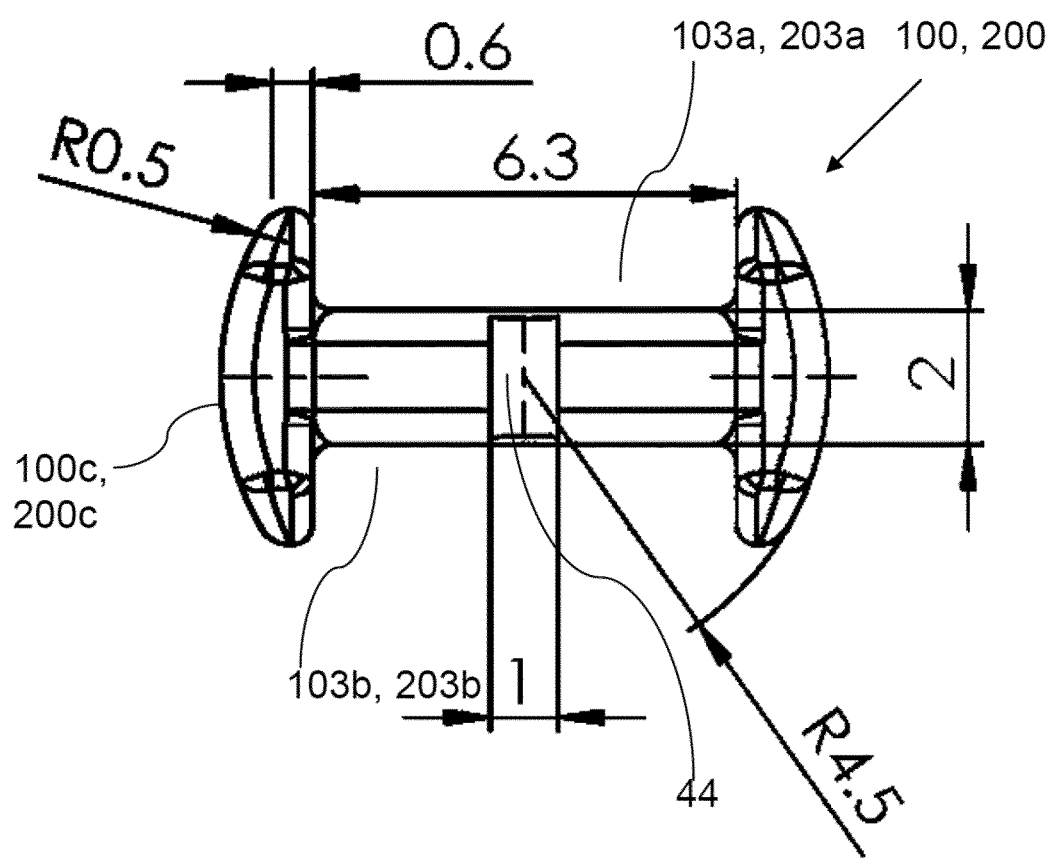
Figure 9:
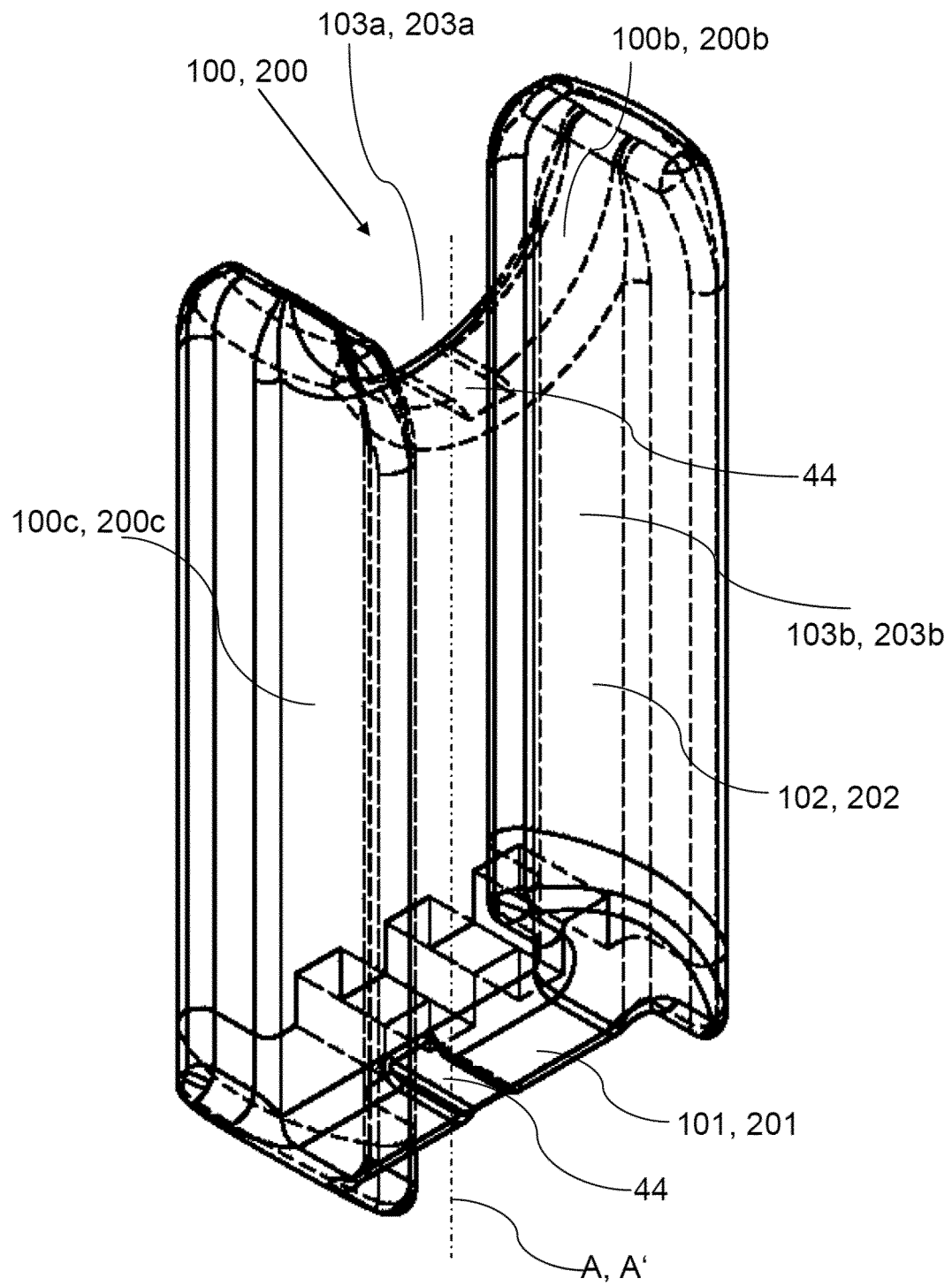
Figure 11:
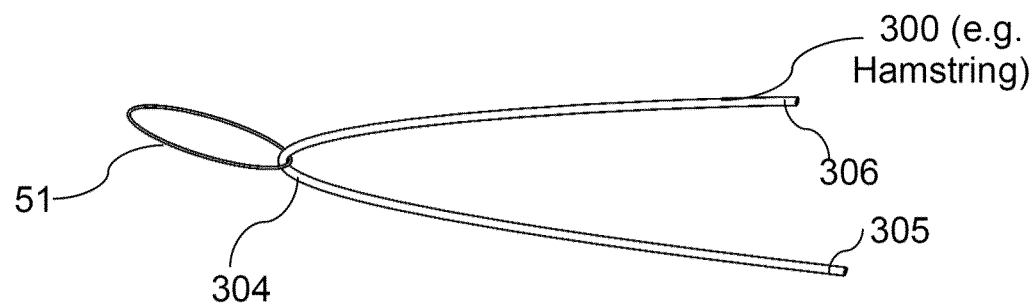
Figure 12:
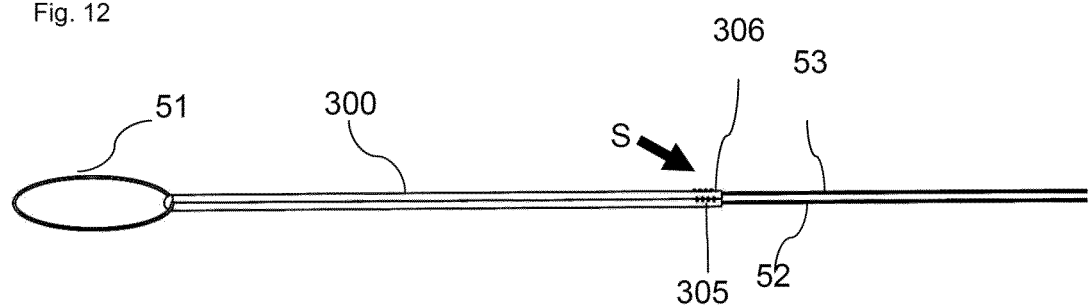
Figure 13:
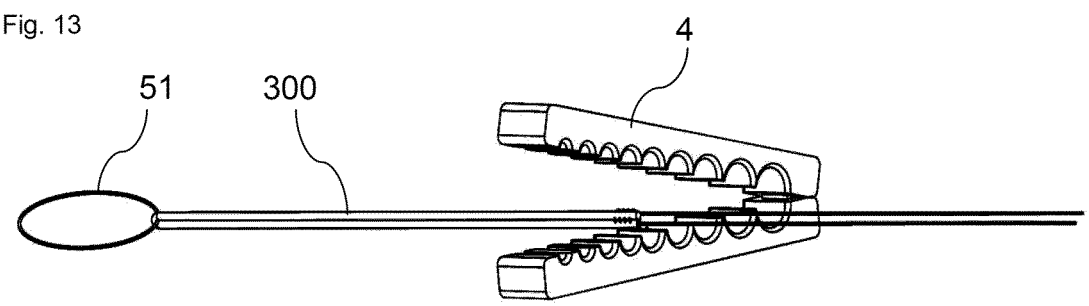

As shown in FIGS. 8 and 9, the first insert 100 comprises a lateral surface 100c extending along the first axis A of the first insert 100, wherein the lateral surface 100c of the first insert 100 is designed to contact the associated bone 2 (e.g. femur) when the first insert 100 is inserted into the bore hole 20 of the associated bone 2. Further, for receiving two strands 303 of the flexible graft 300 (see also above and FIG. 22) the first insert 100 comprises a concave first recess 103a in the form of a furrow, which furrow is formed in said lateral surface 100c and extends along the first axis A. Furthermore, for receiving the other two strands 303 of the flexible graft 300, the first insert 100 comprises a second recess 103b in the form of a furrow, which furrow is also formed in said lateral surface 100c of the first insert 100 and extends along the first axis A on a side of the lateral surface 100c facing away from the first recess 103a. A further face side 100b, namely the second face side 100b of the first insert 100, which faces away from the face side 102a of the insert body 102 to which the cap 101 is attached comprises a concave shape for receiving e.g. those sections of the strands 100 that extend from the first recess 103a over to the second recess 103b (or, in case of the second insert 200, those strand portions that are sutured together behind the second insert 200).

Generally, as shown in FIG. 21, the caps 101, 201 may be entirely omitted and the first or second insert (and particularly also the third insert 400) may be formed in one piece. Here, this osteocondcutive insert part 100 can be either made of a single material, such as hydroxylapatite (HA), tricalcium phosphate(TCP), calcium sulphate, calcium silicate, and related biocompatible derivatives, or can be made out of composite materials, such as TCP/PLA, TCP/PGA, TCP/PLGA, HA/PLA, and related compositions (see also above).

Particularly, in a variant of the embodiment shown in FIG. 21, the first or second insert 100, 200 may comprises a main body 100a, 200a (also denoted as core body) and a layer 100b, 200b (e.g. a coating, particularly forming an outer layer) attached to the main body 100a, 200a, wherein said layer 100b, 200b may completely enclose the main body 100a, 200a of the first or second insert 100, 200.

Particularly, said layer 100b, 200b is formed out of or comprises one of the following substances:
- a polymer, particularly a biocompatible polymer, wherein particularly this polymer is one of: degradable, particularly biodegradable, or non-degradable;
- a copolymer, particularly a biocompatible copolymer, wherein particularly this copolymer is one of: degradable, particularly biodegradable, or non-degradable;
- a combination of different polymers.

Further, particularly said main body 100a, 200a is formed out of or comprises one of the following substances:
- a bioceramics,
- an osteoconductive and/or osteoinductive bioceramics,
- hydroxylapatite,
- tricalcium phosphate,
- calcium sulphate,
- calcium silicate.

Particularly, ideally, there are two functions of the layer or coating. One is to provide strength, the other is sealing (i.e. to prevent particles from the main body 100a, 200a from releasing into e.g. a joint space. FIG. 20 shows further general configurations/shapes that can be assumed by the first or second insert 100, 200 (or by the third insert 400). According to FIG. 20A, the first or second insert 100, 200 merely comprises one (first) recess 103a for receiving e.g. all strands 300. Further as shown in FIG. 20F, the first or second insert 100, 200 does not need to be mirror symmetric and the first and the second recess 103a, 103b can have a different size. Here, the first recess 103a may receive only one strand 303 while the other (second) recess 103b receives e.g. three strands 303.

Further, instead of pronounced recesses, the lateral surface 100c may simply comprise a contact region 104, which particularly according to FIG. 20B and FIG. 20D may comprise a convex bulge for pressing strands 300 of the flexible graft 300 against the bore hole walls. Further, the first or second insert 100, 200 may comprise such contact regions 104 on all sides of the lateral surface 100c, 200c, particularly when the first or second insert 100, 200 is configured to be arranged between the strands 303 as shown for instance in FIG. 20C.

Further, as shown in FIG. 20E, the first or second insert 100, 200 may comprise a cylindrical configuration with a circumferential lateral surface 100c, 200c that encompasses a single first recess 103a, 203a in the form of a through-opening for receiving the flexible graft 300, e.g. all strands 303 of the latter.

Further, as shown in FIG. 20G the first and/or the second insert 100, 200 may also comprise a third and particularly a fourth recess 103c, 103d, 203c, 203d formed in the lateral surface 100c, 200c of the respective insert 100, 200. Here, all four recesses 103a, 103b, 103c, 103d; 203a, 203b, 203c, 203d extend along the axis A of the respective insert 100, 200. Here, the recesses 103a, 103b, 103c, 103d; 203a, 203b, 203c, 203d are preferably equidistantly spaced along the periphery of the respective insert 100, 200. Particularly, in such a configuration the first and/or second insert 100, 200 may comprise a cross-shaped cross section perpendicular to the respective axis A.

Depending on which material is used for the caps 101, 201 (e.g. PEEK) it can be fabricated with the traditional machine tools. However, for the TCP scaffold (first and second insert) 100, 200, the geometry is somewhat complicated and production of which is best suited for injection molding or additive manufacturing techniques. Several materials can be used for the first or second cap 101, 102, but particularly PCL is used as a possible material of choice due to its biodegradability. Here, according to an example of the present invention, an advanced manufacturing technique which combines rapid prototyping and a gel-casting method is used. The negative pattern of a TCP scaffold 100, 200 was designed with a commercial Computer Aided Design (CAD) software (Pro-engineer).

As shown in FIG. 10 the molds were fabricated on a sterolithography apparatus (SPS 600B, xi'an jiaotong university, Xi'an, China) with a commercial epoxy resin (SL, 14120, Huntsman). The CAD data of the negative pattern was converted into STL data by Pro-engineers, imported into Rpdata software, and converted into input file for sterolithography. The molds fabricated were then cleaned with isopropanol alcohol. TCP powders along with monomers (acrylamide, methylenebisacrylamide), dispersant (sodium polymethacrylate) was mixed with DI water to form the ceramic slurry. Table 1 shows the amount of chemicals added to DI water to formulate the ceramic slurry.

TABLE 1

Composition of slurry for scaffold fabrication

| | Component | Amount |
|---|---|---|
| Solvent: | Deionized water | 35 g |
| Ceramic powder: | Beta-tricalcium phosphate | 60 g |
| Monomer: | Acrylamide | 4 g |
| Cross linker: | Methylenebisacrylamide | 0.5 g |
| Dispersant: | Sodium polymethacrylate | 0.6 g |
| Initiator: | Ammonium persulphate | 0.2 g |
| Catalyst: | N,N,N'N'-tetramethylethylenediamine | 0.1 g |

The slurry prepared was deagglomerated by ultrasonic for 5 hours and subsequently deaired under vacuum until no further release of air bubbles from the sample. Catalyst (ammonium persulphate) and initiator (N,N,N'N'-tetramethylethylenediamine) were added to the slurry to polymerize the monomers. The amount of which were controlled to allow a sufficient time for casting process. The TCP slurry was cast into the molds under vacuum to force the TCP powders to migrate into the interspaces of the paraffin spheres. The samples were dried at the room temperature for 72 hours. After the drying, pyrolysis of the epoxy resin molds and paraffin spheres were conducted in air in an electric furnace with a heating rate of 5° C./h from room temperature to 340° C., holding 5 hours at 340° C. to ensure most paraffin spheres were burn out, and then sintered to 660° C. at a rate of 10° C./h, holding 5 hours at 660° C. to ensure most epoxy resin was burn out. After that the heating rate went up to 60° C./h till 1200° C., holding 5 hours at 1200° C., and then decreased to room temperature in 48 hours.

In a next step, a PCL gel casting for the cap-part (first or second cap) 101, 102 was done using the same 3-D printing techniques and mold resin materials mentioned above. PCL is a biologically absorbable and biocompatible material which is used in many medical applications. After insertion of PCL (Shanghai Leon Chemical Ltd, China), the sintered TCP part was laid above, so that the rills (protrusions P and recesses R) of both parts 100, 101; 200, 201 intersect. This procedure allows a rigid fixation and bonding of those two parts and is robust against shear and torque forces.

After hardening, the hybrid mold can be removed and sterilized by gamma sterilization (Co60). In FIG. 10 the different production steps are displayed.

Further, FIG. 10 also indicates a possibility of connecting the first elongated flexible element 41 to the first insert 100, namely by looping it around the insert body 102, to which the cap 101 is then connected by casting it to the insert body 102 so that the flexible element 41 is enclosed by the insert body and the cap 101 in a form-fitting manner (this technique can be applied to all inserts described herein).

While the graft preparation is preferably based on the hamstring tendon graft preparation technique, the insertion technique is particularly comparable to the BTB graft implantation technique. For this technique, biodegradable suture knots (e.g. Ethibond, Ethicon Inc., Somerville, USA) are used to suture the quadrupled autograft 300 intraligamentarty, while high resistant nonabsorbable braided sutures (e.g. FiberWire, Arthrex, Naples, USA) 41, 42, 51, 52, 53 are used to hold both ends of external fixation devices (e.g. plate members 43, 54) and the hybrid-insert-autograft-bundle 100, 300, 200, using e.g. baseball stitches.

The surgical procedure does nonessentially differ from the BTB-graft implantation method and can be done, using standard medial and lateral parapatellar arthroscopy portals. After removing the torn ACL, a 6 mm tunnel is drilled over the footprint of the femoral and tibial attachment of the removed ACL. According to the previously, during graft preparation, measured diameter of graft-bundle and length, the femoral tunnel gets concentrically reamed to the certain measured length and diameter. The tunnel can be circular, and can also be non-circular, such as oval according to the graft size and geometry, shown in FIG. 22. A specialized drilling tool is adopted. On the tibial side the initial bore hole gets reamed on its whole length (cf. FIG. 23). In a next step, the whole graft-bundle gets pulled through tibia, joint space and femur (cf. FIG. 24, left hand side) until the external fixation device or plate member 43 (e.g Fliptack, Karl Storz, Tuttlingen, Germany) can be flipped on the cortical bone, so that it seizes by tension on the outer side of the femoral bore hole (cf. FIG. 24, right hand side). In a last step, a second internal (e.g. screw) 55 and/or external fixation device, e.g. a plate member, 54 (e.g. Endotack, Karl Storz, Tuttlingen, Germany) on the tibial side is inserted in the tibial borehole (screw 55) or butts against the outer side of the tibial bore hole (external fixation device 54) under constant tension of the graft-bundle 300 (cf. FIG. 25) [7].

As further shown in FIG. 26, the (e.g. hybrid) second insert 200 in the tibia part 3 can be mounted in an axial flexible way. During implantation, the second insert 200 in tibia tunnel can be pulled by additional sutures S' attached to the second insert 200. With the arthroscopy view, the (hybrid) second insert 200 in the tibia tunnel 30 can be adjusted into the perfect position.

To implant the tendon graft 300 through the medial side of the joint is also a possible choice (cf. FIG. 27). In this case, the tibia tunnel 30 can be drilled in similar condition as femoral tunnel, with larger tunnel for the graft 300 and smaller tunnel for the sutures 42, 51, 52, 53. This kind of tibia tunnel 30 can be achieved by "RetroDrill" technique by Arthrex. The (hybrid) first and second insert 100, 200 with different structures as mentioned above with barbs, pins, anchors, etc. will work compatible with this implantation procedure.

Further, as shown in FIG. 31 the medical implant device 1 according to the invention may also comprise a third insert 400 that may comprise the individual features described

| Tendon size | | | | Hybrid insert | Bone tunnel | | | compression degree | |
|---|---|---|---|---|---|---|---|---|---|
| Measured | Max | Min | | size | size | | Residue | 1st | 2nd |
| ϕ (mm) | area (mm$^2$) | area (mm$^2$) | area (mm$^2$) | ϕ (mm) | ϕ (mm) | Comment | area[1] (mm2) | measurement[2] | measurement[3] |
| 7.5 | 44.18 | 51.92 | 25.96 | 8.5 | 9 | Medium | 41.86 | 30% | 38% |
| 8 | 50.27 | 56.43 | 28.22 | 9 | 9.5 | Loose | 46.4 | 22% | 36% |
| 8.5 | 56.74 | 67.39 | 33.7 | 9.5 | 10 | Tight | 51.61 | 32% | 47% |
| 9 | 63.62 | 80 | 40 | 10 | 10.5 | Tight | 56.42 | 41% | 59% |

[1]Residue area of the hybrid insert filled tunnel
[2]Tendon measurement process
[3]Insertion process The dimension of the (e.g. osteoconductive) first or second insert 100, 200 is chosen based on the size of the tendon graft. The co-relation of the tendon size, insert size and bone tunnel size which may be used in the present invention is shown in the following table.

herein for the first and the second insert 100, 200. Preferably, the third insert 400 is connected to a central region 450 the flexible graft 300 such that two bundles (or sections) 300a, 300b of the flexible graft 300 extend from the third insert 400, which two bundles 300a, 300b are connected to the first and the second insert 100, 200.

In detail, the graft 300 is folded at a middle section 304 as shown in detail A of FIG. 31, which middle section 304 runs through the loop formed by the second elongated flexible member 42 (cf. also FIG. 1). Thus, two sections 300a, 300b each comprising two strands 303 of the graft 300 extend from the first insert 100 to the third insert 400, wherein each strand 303 is arranged in an associated recess 103a, 103b of the first insert 100, namely in a first recess 103a and a second recess 103b that faces away from the first recess 103a of the first insert 100. Further the strands 303 are laid around the third insert 400 such that two strands 303 are arranged in a first recess 403a of the third insert 400 as well as in a second recess 403b of the third insert 400, which second recess 403b of the third insert 400 in turn faces away from the first recess 403a of the third insert 400 (as also shown in FIG. 22 for instance). From the third insert 400, the two strands 303 run to the second insert 200 where the first and second end section 305, 306 of the graft 300/strands 303 are connected to the second insert 200 by means of sutures S. Also here, one strand 303 (first end section 305) is arranged in the first recess 203a of the second insert 200 while the other strand 303/second end section 306 of the graft 300 is arranged in the second recess 203b of the second insert 200, wherein the first recess 203a of the second insert faces 200 away from the second recess 203b of the second insert 200.

The third insert 400 may be connected to a third (external) fixation means 60 that is particularly designed and connected to the third insert 400 as the first fixation 40 means shown in FIG. 1. Further, the first insert 100 is connected to a first fixation means 40 corresponding to the first fixation means 40 shown in FIG. 1. Further, the elongated flexible members 51, 52 form part of a second fixation means 50 that may also comprise a plate member 54 as shown in FIG. 1

In this so called double bundle reconstruction technique, the third insert 400 is particularly inserted into a non-circular cylindrical bore hole 20 of the femur 2, while the first and the second insert 100, 200 are inserted into neighbouring bore holes 30 of the tibia 3.

Further, examples of the present invention were performed with two healthy adult male pigs (Chinese tri-hybrid pig: Xianyang breed) aged around four months and weighing 47±3 kg (mean±SD) at time of surgery. ACL reconstructions were performed on the left knee. The pigs were thoroughly disinfected by spraying with 0.25% didecyl dimethyl ammonium bromide solution two days before surgery. Antibiotics (Penicillin of 800'000 U) were given to each pig by intramuscular injection twice the day before the operation. A sodium pentobarbital solution of 3.5% concentration was used as anesthetic. Each animal was given 0.5 ml/kg by abdominal injection, and followed 5 minutes later with additional 0.2 ml/kg dose by venous injection. The animal was then positioned supine on the operating table in a specially designed constraint. The left hindleg was shaved, and thoroughly washed with povidone-iodine solution. An open surgical procedure for ACL reconstruction was used as previously described using the porcine distal femora flexor tendon as an autograft (cf. FIG. 28). Radiological observation using standard c-arm device was performed on the two pigs right after the operation. Radiographs show that the technique is technically applicable and that all particular implant parts are well-positioned (FIGS. 29 and 30).

REFERENCES

1. Wen, C. Y., et al., The Use of Brushite Calcium Phosphate Cement for Enhancement of Bone-Tendon Integration in an Anterior Cruciate Ligament Reconstruction Rabbit Model. Journal of Biomedical Materials Research Part B-Applied Biomaterials, 2009. 89B(2): p. 466-474.
2. Huangfu, X. Q. and J. Z. Zhao, Tendon-bone healing enhancement using injectable tricalcium phosphate in a dog anterior cruciate ligament reconstruction model. Arthroscopy-the Journal of Arthroscopic and Related Surgery, 2007. 23(5): p. 455-462.
3. Soon, M. Y. H., et al., An analysis of soft tissue allograft anterior cruciate ligament reconstruction in a rabbit model—A short-term study of the use of mesenchymal stem cells to enhance tendon osteointegration. American Journal of Sports Medicine, 2007. 35(6): p. 962-971.
4. Lim, J. K., et al., Enhancement of tendon graft osteointegration using mesenchymal stem cells in a rabbit model of anterior cruciate ligament reconstruction. Arthroscopy-the Journal of Arthroscopic and Related Surgery, 2004. 20(9): p. 899-910.
5. Rodeo, S. A., et al., Use of recombinant human bone morphogenetic protein-2 to enhance tendon healing in a bone tunnel. American Journal of Sports Medicine, 1999. 27(4): p. 476-488.
6. Yu, Y., et al., Bone morphogenetic proteins and Smad expression in ovine tendon-bone healing. Arthroscopy-the Journal of Arthroscopic and Related Surgery, 2007. 23(2): p. 205-210.
7. Borbas, P., et al., Radiodense ligament markers for radiographic evaluation of anterior cruciate ligament reconstruction. The Knee, 2014.

The invention claimed is:

1. A medical implant device (1) for attaching a flexible graft (300) to a bone (2, 3), comprising:
at least a first insert (100) comprising a synthetic osteoconductive and/or osteoinductive material, the first insert (100) extends along a first axis (A), wherein the first insert (100) is designed to be inserted into a bore hole (20) of an associated bone (2) in an insertion direction aligned with the first axis (A), and wherein the first insert (100) comprises a lateral surface (100c) extending along the first axis (A) of the first insert (100), wherein the lateral surface (100c) of the first insert (100) is designed to contact its associated bone (2) when the first insert (100) is inserted into the bore hole (20) of its associated bone (2), and wherein the first insert (100) comprises a first recess (103a) in the form of a furrow, which furrow is formed in said lateral surface (100c) of the first insert (100) and extends along the first axis (A), and wherein the first insert (100) comprises a second recess (103b) in the form of a furrow, which furrow is formed in said lateral surface (100c) of the first insert (100) and extends along the first axis (A), and wherein said second recess (103b) of the first insert (100) is formed on a side of the lateral surface (100c) of the first insert (100) facing away from the first recess (103a) of the first insert (100)
a first elongated flexible member (41) and a second elongated flexible member (42) for fixing the first insert (100) to its associated bone (2), wherein the first elongated flexible member (41) is looped around the first insert (100), and wherein the second elongated flexible member (42) is connected to the first elongated flexible member (41), wherein the second elongated flexible member (42) is laid around the first elongated flexible member (41), and wherein the second elongated flexible member (42) is connected to a plate member (43), which plate member (43) is designed to butt against said associated bone (2), and
a flexible graft (300), wherein the flexible graft (300) is connected to the at least one first insert (100) wherein the flexible graft (300) is an elongated member that is folded at least once so that the flexible graft (300) comprises a plurality of strands (303) extending along each other, wherein at least one strand (303) is arranged in said first recess (103a) of the first insert (100), and wherein at least one strand (303) is arranged in said second recess (103b) of the first insert (100), and wherein the flexible graft (300) is laid around the first insert (100), wherein the flexible graft (300) is threaded through a loop formed by the second elongated flexible member (42).

2. The medical implant device according to claim 1, characterized in that the medical implant device (1) further comprises a second insert (200) comprising a synthetic osteoconductive and/or osteoinductive material, wherein the flexible graft (300) comprises a first end region (301) and a second end region (302), and wherein the first insert (100) is connected to the first end region (301), and wherein the second insert (200) is connected to the second end region (302).

3. The medical implant device according to claim 1, characterized in that the first insert (100) comprises one of the following substances: hydroxylapatite (HA), tricalcium phosphate (TCP), calcium sulphate, calcium silicate.

4. The medical implant device according to claim 2, characterized in that the second insert (200) extends along a second axis (A'), wherein the second insert (200) is designed to be inserted into a bore hole (30) of an associated bone (3) in an insertion direction aligned with the second axis (A').

5. The medical implant device according to claim 1, characterized in that the first insert (100) comprises a first region (101) forming a first face side (100a) of the first insert (100) and an adjacent second region (102) forming a second face side (100b) of the first insert (100), wherein the two face sides (100a, 100b) of the first insert (100) face away from each other.

6. The medical implant device according to claim 5, characterized in that the first region (101) of the first insert (100) comprises one of the following substances:
a polymer,
a biocompatible polymer,
a degradable biocompatible polymer,
a biodegradable biocompatible polymer,
a non-degradable biocompatible polymer
a copolymer,
a biocompatible copolymer,
a degradable biocompatible copolymer,
a biodegradable biocompatible copolymer,
a non-degradable biocompatible copolymer,
a combination of different polymers,
polyactic acid (PLA),
poly(lactic-co-glycolic acid),
polyglutamic acid (PGA),
poly-ε-caprolactone (PCL),
polyhydroxyalkanoate (PHA),
polyether ether ketone (PEEK),
a biocompatible derivative related to at least one of the above stated substances;
a titanium alloy;
a stainless steel;
a composite of a polymer,
a composite of a biocompatible polymer,
a bioceramics;
a composite comprising PLA and TCP;
a composite comprising PLA and HA;
a composite comprising PCL and TCP;
a composite comprising PCL and HA.

7. The medical implant device according to claim 5, characterized in that the second region (102) of the first insert (100) comprises one of the following substances:
a bioceramics,
an osteoconductive and/or osteoinductive bioceramics,
hydroxylapatite,
tricalcium phosphate,
calcium sulphate,
calcium silicate.

8. The medical implant device according to claim 5, characterized in that the first region (101) of the first insert (100) is formed as a cap (101), and the second region (102) of the first insert (100) is formed as an insert body (102) for supporting bone regeneration, wherein the cap (101) of the first insert (100) is connected to a face side (102a) of the insert body (102) of the first insert (100).

9. The medical implant device according to claim 5, characterized in that the first region (101) of the first insert (100) is designed to provide a resistance to a movement of the first insert (100) counter to its insertion direction when the first insert (100) is inserted into the bore hole (20) of its associated bone (2).

10. The medical implant device according to claim 1, characterized in that the first insert (100) comprises a main body (100a) and a layer (100b) attached to the main body (100a).

11. The medical implant device according to claim 10, characterized in that said layer (100b) of the first insert (100) completely encloses the main body (100a) of the first insert (100).

12. The medical implant device according to claim 10, characterized in that the layer (100b) of the first insert (100) is formed out of or comprises one of the following substances:
a polymer,
a biocompatible polymer,
a degradable biocompatible polymer,
a biodegradable biocompatible polymer,
a non-degradable biocompatible polymer,
a copolymer,
a biocompatible copolymer,
a degradable biocompatible copolymer,
a biodegradable biocompatible copolymer,
a non-degradable biocompatible copolymer,
a combination of different polymers.

13. The medical implant device according to claim 10, characterized in that the main body (100a) of the first insert (100) comprises one of the following substances:
a bioceramics,
an osteoconductive and/or osteoinductive bioceramics,
hydroxylapatite,
tricalcium phosphate,
calcium sulphate,
calcium silicate.

14. The medical implant device according to claim 10, characterized in that, the layer (100b) of the first insert (100) is designed to be degradable such that it degrades within a pre-defined period of time after implantation of the medical implant device into the body of a patient.

15. The medical implant device according to claim 10, characterized in that the layer (100b) of the first insert (100) is adapted to strengthen the main body (100a) of the first insert (100).

16. The medical implant device according to claim 13, characterized in that the layer (100b) of the first insert (100) is adapted to seal off the main body (100a) of the first insert (100) so as to prevent release of said substance from the main body (100a) of the first insert (100).

17. The medical implant device according to claim 1, wherein the flexible graft (300) is folded at least two times so that the flexible graft (300) comprises at least four strands (303) extending along each other.

18. The medical implant device according to claim characterized in that the second insert (200) comprises a lateral surface (200c) extending along the second axis (A') of the second insert (200), wherein the lateral surface (200c) of the second insert (200) is designed to contact its associated bone (3) when the second insert (200) is inserted into the bore hole (30) of its associated bone (3).

19. The medical implant device according to claim 18, characterized in that, the second insert (200) comprises a first recess (203a) in the form of a furrow, which furrow is formed in said lateral surface (200c) of the second insert (200) and extends along the second axis (A'), wherein at least one strand (303) is arranged in said first recess of the second insert (200).

20. The medical implant device according to claim 2, characterized in that the second insert (200) comprises a second recess (203b) in the form of a furrow, which furrow is formed in said lateral surface (200c) of the second insert (200) and extends along the second axis (A'), wherein at least one strand (303) is arranged in said second recess (203b) of the second insert (200), wherein said second recess (203b) of the second insert (200) is formed on a side of the lateral surface (200c) of the second insert (200) facing away from the first recess (203a) of the second insert (200).

* * * * *